US012329466B2

United States Patent
Martin, III et al.

(10) Patent No.: US 12,329,466 B2
(45) Date of Patent: *Jun. 17, 2025

(54) SYSTEM AND METHODS FOR PLANNING AND PERFORMING THREE-DIMENSIONAL HOLOGRAPHIC INTERVENTIONAL PROCEDURES WITH THREE-DIMENSIONAL TOMOGRAPHIC AND LIVE IMAGING

(71) Applicant: MEDIVIEW XR, INC., Cleveland, OH (US)

(72) Inventors: Charles Martin, III, Pepper Pike, OH (US); Jeffrey H. Yanof, Solon, OH (US); Karl West, Geneva, OH (US); Mina S. Fahim, New Brighton, MN (US); John Black, Napoleon, OH (US)

(73) Assignee: MEDIVIEW XR, INC., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/771,176

(22) Filed: Jul. 12, 2024

(65) Prior Publication Data

US 2024/0358446 A1  Oct. 31, 2024

Related U.S. Application Data

(63) Continuation of application No. 18/318,539, filed on May 16, 2023, now Pat. No. 12,059,216, which is a
(Continued)

(51) Int. Cl.
*G06K 9/00* (2022.01)
*A61B 34/20* (2016.01)
(Continued)

(52) U.S. Cl.
CPC .............. *A61B 34/20* (2016.02); *A61B 90/37* (2016.02); *G02B 27/0172* (2013.01);
(Continued)

(58) Field of Classification Search
CPC . A61K 35/12; G06K 9/00; G06T 3/20; A61B 34/20
(Continued)

(56) References Cited

U.S. PATENT DOCUMENTS

| 2006/0149147 A1* | 7/2006 | Yanof | A61B 90/50 606/130 |
| 2014/0247918 A1* | 9/2014 | Kang | A61B 6/4405 378/62 |

(Continued)

FOREIGN PATENT DOCUMENTS

CN  109996511 A  7/2019

OTHER PUBLICATIONS

Microsoft HoloLens, website, https://www.microsoft.com/en-us/hololens.

*Primary Examiner* — Seyed H Azarian
(74) *Attorney, Agent, or Firm* — Jacob M. Ward; Ward Law Office LLC

(57) ABSTRACT

A method and a system for image-guided intervention such as a percutaneous treatment or diagnosis of a patient may include at least one of a pre-registration method and a re-registration method. The pre-registration method is configured to permit for an efficient virtual representation of a planned trajectory to target tissue during the intervention, for example, as a holographic light ray shown through an augmented reality system. In turn, this allows the operator to align a physical instrument such as a medical probe for the intervention. The re-registration method is configured to adjust for inaccuracy in the virtual representation generated
(Continued)

by the pre-registration method, as determined by live imaging of the patient during the intervention. The re-registration method may employ the use of intersectional contour lines to define the target tissue as viewed through the augmented reality system, which permits for an unobstructed view of the target tissue for the intervention.

13 Claims, 11 Drawing Sheets

Related U.S. Application Data continuation of application No. 17/117,841, filed on Dec. 10, 2020, now Pat. No. 11,701,183.

(60) Provisional application No. 62/945,983, filed on Dec. 10, 2019.

(51) Int. Cl.
| | |
|---|---|
| *A61B 90/00* | (2016.01) |
| *A61K 35/12* | (2015.01) |
| *G02B 27/01* | (2006.01) |
| *G06T 7/00* | (2017.01) |
| *G06T 19/00* | (2011.01) |

(52) U.S. Cl.
CPC .......... *G06T 7/0012* (2013.01); *G06T 19/006* (2013.01); *A61B 2034/2055* (2016.02); *A61M 2205/507* (2013.01); *G02B 2027/0174* (2013.01); *G06T 2210/41* (2013.01)

(58) Field of Classification Search
USPC ................ 382/100, 103, 106–107, 128–132, 382/151–153, 168, 173, 181, 193, 199, 382/209, 224, 254, 276, 291, 312, 321; 348/47; 600/130, 417; 378/62
See application file for complete search history.

(56) References Cited

U.S. PATENT DOCUMENTS

| | | | | |
|---|---|---|---|---|
| 2015/0351860 | A1* | 12/2015 | Piron | A61B 5/065 |
| | | | | 600/417 |
| 2016/0191887 | A1* | 6/2016 | Casas | H04N 13/156 |
| | | | | 348/47 |
| 2018/0303377 | A1 | 10/2018 | West et al. | |
| 2018/0303563 | A1* | 10/2018 | West | A61B 90/37 |
| 2019/0339525 | A1* | 11/2019 | Yanof | A61B 8/466 |

\* cited by examiner

Determining the intersection US plane and CT Surface mesh

Normal Vector to US Tplane = (Nx, Ny, Nz) = Ni
Point on US Plane lane = (Px1, Py1, Pz1) = Pi1
Test Point on Surface = (Px, Py, Pz) = Pi Px1 Nx + Px2 Ny + Px3 Nz = Px Nx + Py Ny + Pz Nz 0 = Nx * Px + Ny * Py + Nz * Pz - (Nx Px1 + Ny Px2 + Nz Px3)

0 = Nx (Px – Px1) + Ny (Py-Py1) + Nz (Pz-Pz1) on the US plane

If Dot (Ni, Pi-Pi1) + lamda > 0
then it's not on or near the US plane, don't show

SYSTEM AND METHODS FOR PLANNING AND PERFORMING THREE-DIMENSIONAL HOLOGRAPHIC INTERVENTIONAL PROCEDURES WITH THREE-DIMENSIONAL TOMOGRAPHIC AND LIVE IMAGING

CROSS REFERENCE TO RELATED APPLICATIONS

This application is a continuation of U.S. Continuation application Ser. No. 18/318,539 filed on May 16, 2023, which claims the benefit of U.S. application Ser. No. 17/117,841 filed on Dec. 10, 2020, and claims the benefit of U.S. Provisional Application Ser. No. 62/945,983, filed on Dec. 10, 2019. The entire disclosures of the above applications are incorporated herein by reference.

FIELD

The present disclosure relates to holographic augmented reality applications and, more particularly, medical applications employing holographic augmented reality.

INTRODUCTION

This section provides background information related to the present disclosure which is not necessarily prior art.

Holographic augmented reality technology is finding more widespread use in healthcare applications to improve medical procedures, clinical outcomes, and long-term patient care. These augmented reality technologies are also useful for enhancing the real environments in the patient care setting, for example, with content-specific information to improve patient outcomes. For example, a practitioner can view additional information in the same field of view while performing a medical procedure, where the practitioner does not have to change their gaze, which may otherwise slow down or reduce the efficiency of the procedure.

More specifically, image-guided intervention during medical procedures such as minimally invasive surgical (MIS) procedures is inherently a highly three-dimensional (3D) task. For example, percutaneous ablation of solid tumors requires accurate 3D positioning of one or more thermal probes while the tumor is undergoing respiratory motion or ventilation. However, flat or two-dimensional (2D) display monitors are often used to display the image-guidance data in the standard of care for MIS procedures. 3D holographic guidance and navigation, using one or more imaging modalities, can provide improved depth perception and spatial understanding during image-guided intervention, but the spatial registration of 3D guidance and navigation holograms must be more 1) accurate and 2) easy to use (i.e., operator workflow must be effective and efficient) for these methods to be adopted relative to more invasive surgery.

As described in U.S. Patent Application Publication No. 2018/0303563 to West et al., it is known to use 3D holographic image-guidance to track an interventional device during a percutaneous procedure. The 3D holographic image-guidance can be provided by a head-mounted device by transforming tracking data and body image data to a common coordinate system and creating a holographic display relative to a body of a patient to track the interventional device during the non-vascular percutaneous procedure. The holographic display can also include graphics to provide guidance for the physical interventional device as it travels through the anatomy of the patient.

There is a continuing need for a holographic system and method that enables pre-registration for 3D holographic guidance and navigation leading to less steps for the operator and more effective workflow, thereby facilitating increased adoption of the system and method. Desirably, the system and method enable intra-procedural re-registration of 3D holograms derived from 3D tomographic data with live imaging to improve accuracy and safety of the probe placement during the MIS procedure.

SUMMARY

In concordance with the instant disclosure, a holographic system and method that enables pre-registration for 3D holographic guidance and navigation leading to less steps for the operator and more effective workflow, thereby facilitating increased adoption of the system and method, and which enables intra-procedural re-registration of 3D holograms derived from 3D tomographic data with live imaging to improve accuracy and safety of the probe placement during the MIS procedure, has been surprisingly discovered.

In one embodiment, a system and method of image-guided intervention for a patient involving pre-registration includes provision of an installation of an augmented reality system such as a Microsoft HoloLens® at a first image acquisition apparatus. The augmented reality system is in communication with a computer having a processor and a memory, and the computer may be integrated with augmented reality system. The augmented reality system may initially be disposed at a predetermined storage position. The augmented reality system has an augmented reality system coordinate system and the first image acquisition apparatus has a first image acquisition apparatus coordinate system. The first image acquisition apparatus further has a patient table for receiving a patient and an imager for acquiring a first holographic image dataset from the patient while on the patient table.

The installation further includes a step of placing a first optical image target at a predetermined location on the imager. First optical image target coordinates are then acquired from the first optical image target with the augmented reality system. A pre-registration transformation of the first image acquisition apparatus coordinate system into the augmented reality system coordinate system is then determined using the first optical image target coordinates. The pre-registration transformation is stored in the memory of the computer, whereby a pre-registration of the first image acquisition apparatus with the augmented reality system is performed during the installation.

Following the installation of the augmented reality system and the pre-registration of the first image acquisition apparatus with the augmented reality system, the method further includes a step of applying the pre-registration transformation to the first holographic image dataset. This transforms the first holographic image dataset from the first image acquisition apparatus coordinate system to the augmented reality system coordinate system.

Advantageously, this instance of the pre-registration can be used repeatably and improves the efficiency of the operator performing the image-guided intervention by eliminating certain registration procedures that would otherwise need to be performed while the patient is on the table for the image-guided intervention.

In another embodiment, a system and a method of image-guided intervention for a patient involving re-registration includes provision of an installation of an augmented reality system such as a Microsoft HoloLens® at a first image acquisition apparatus. The augmented reality system is in communication with a computer with a processor and a memory. The augmented reality system may initially be disposed at a predetermined storage position. The augmented reality system has an augmented reality system coordinate system and the first image acquisition apparatus has a first image acquisition apparatus coordinate system. An initial transformation, such as, but not limited to, a pre-registration transformation of the first image acquisition apparatus coordinate system into the augmented reality system coordinate system, is stored in the memory of the computer. The first image acquisition apparatus further has a patient table for receiving a patient and an imager for acquiring a first holographic image dataset from the patient while on the patient table.

The method further includes a step of acquiring with one of the first image acquisition apparatus and a second image acquisition apparatus a real-time holographic image dataset of the patient during the image-guided intervention. The real-time holographic image dataset is then compared with the patient or the first holographic image dataset. The first holographic image dataset is then adjusted, either manually by the operator or automatically according to predetermined rules, to align the first holographic image dataset with the real-time holographic image dataset from the patient. This adjustment thereby provides a re-registration transformation. The re-registration transformation may be stored in the memory of the computer.

In a further embodiment, a system and a method of image-guided intervention for a patient involving an intersectional contour is provided. The intersectional contour technique may be employed as part of a re-registration system and a method as described, or may be used in other contexts relative to the image-guided intervention, as desired. The method includes a step of acquiring with a first image acquisition apparatus a first holographic image dataset of the patient, and acquiring with a second image acquisition apparatus a second holographic image dataset of the patient during the image-guided intervention. The first holographic image dataset is then compared with the second holographic image dataset, for example, by overlaying the first holographic image dataset with the second holographic image dataset. The intersectional contour of the first holographic image dataset on the second holographic image dataset is then determined. A portion of the first holographic image dataset that is not the intersectional contour may then be removed from a view of an operator of the augmented reality system. Only the intersectional contour of the first holographic image dataset is thereby shown overlaid on the second holographic image dataset via the augmented reality system.

Further areas of applicability will become apparent from the description provided herein. It should be understood that the description and specific examples are intended for purposes of illustration only and are not intended to limit the scope of the present disclosure.

DRAWINGS

The drawings described herein are for illustrative purposes only of selected embodiments and not all possible implementations and are not intended to limit the scope of the present disclosure.

Figures 13, 14:
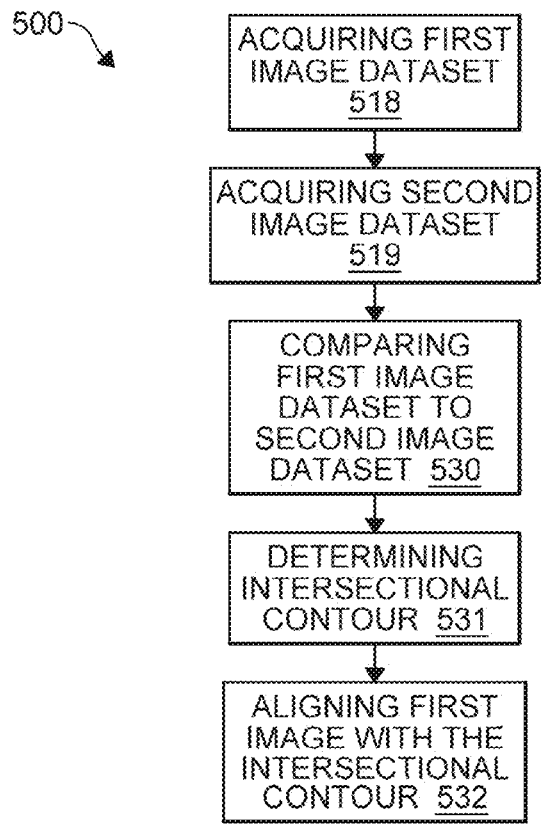
FIG. 13 is a flow diagram illustrating a method for generation of an intersectional contour for a re-registration associated with an image-guided intervention for a patient, according to a further embodiment of the disclosure.
FIG. 14 is a table depicting an algorithm for the generation of the intersectional contour of FIG. 13, according to the further embodiment of the disclosure.
Figure 15:
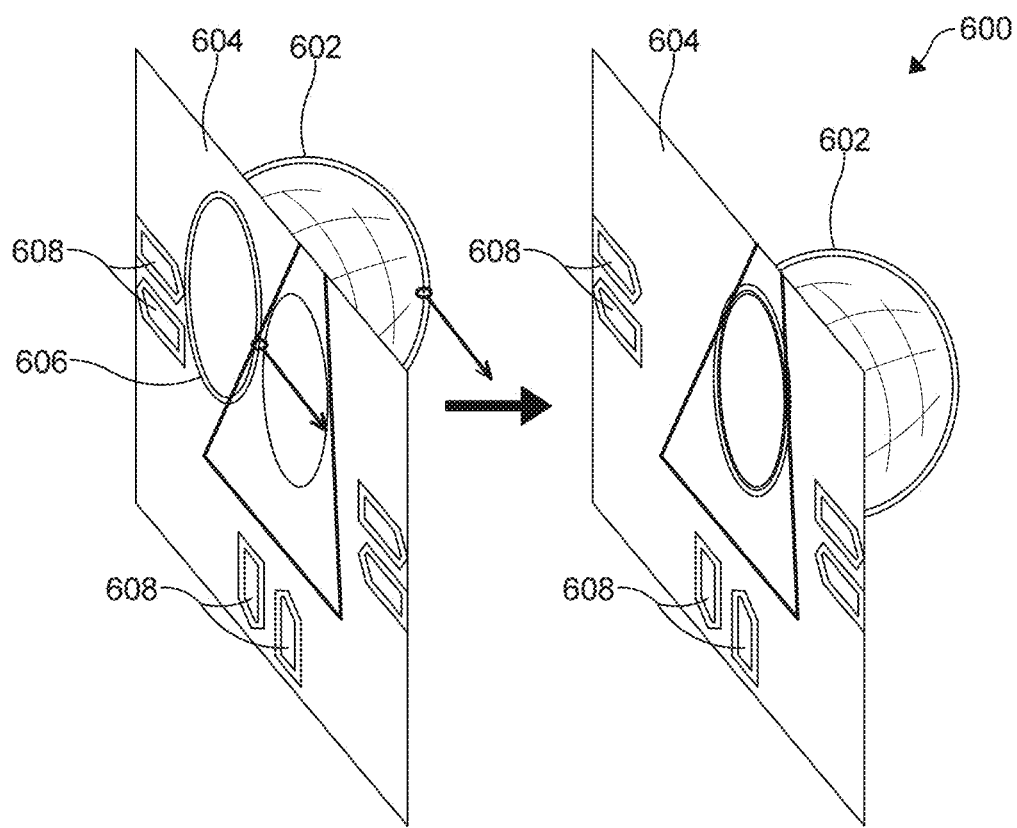
Figure 16:
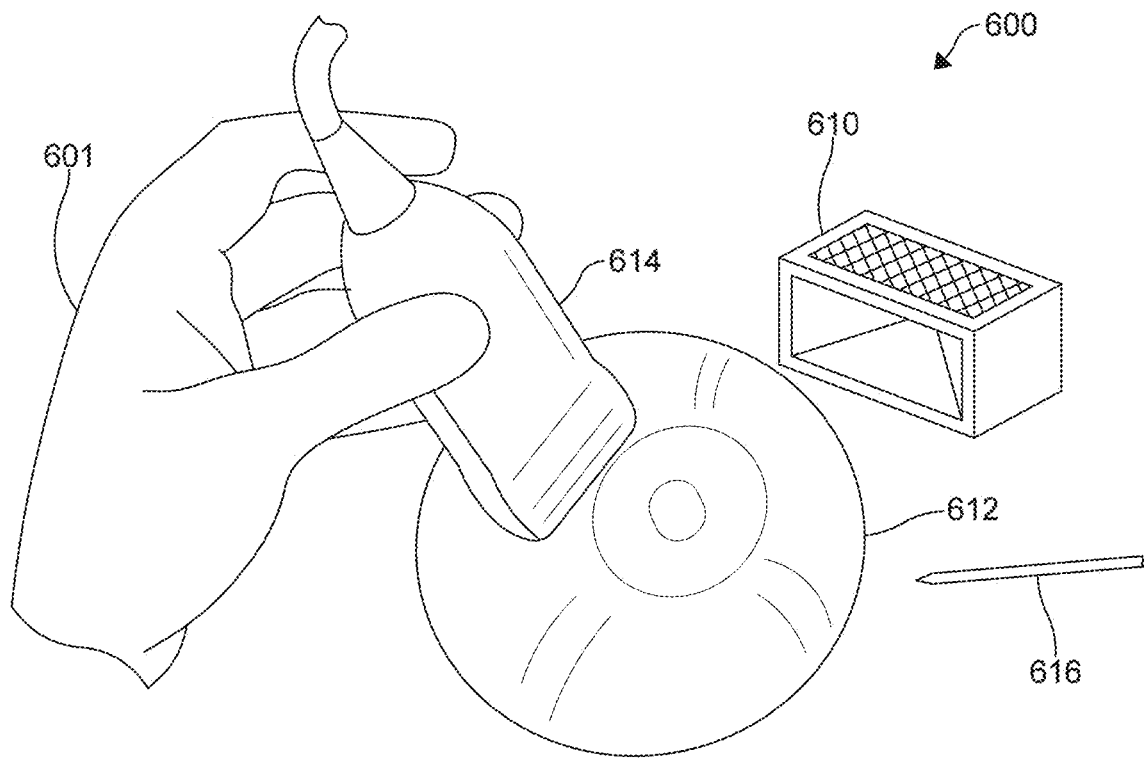
Figure 17:
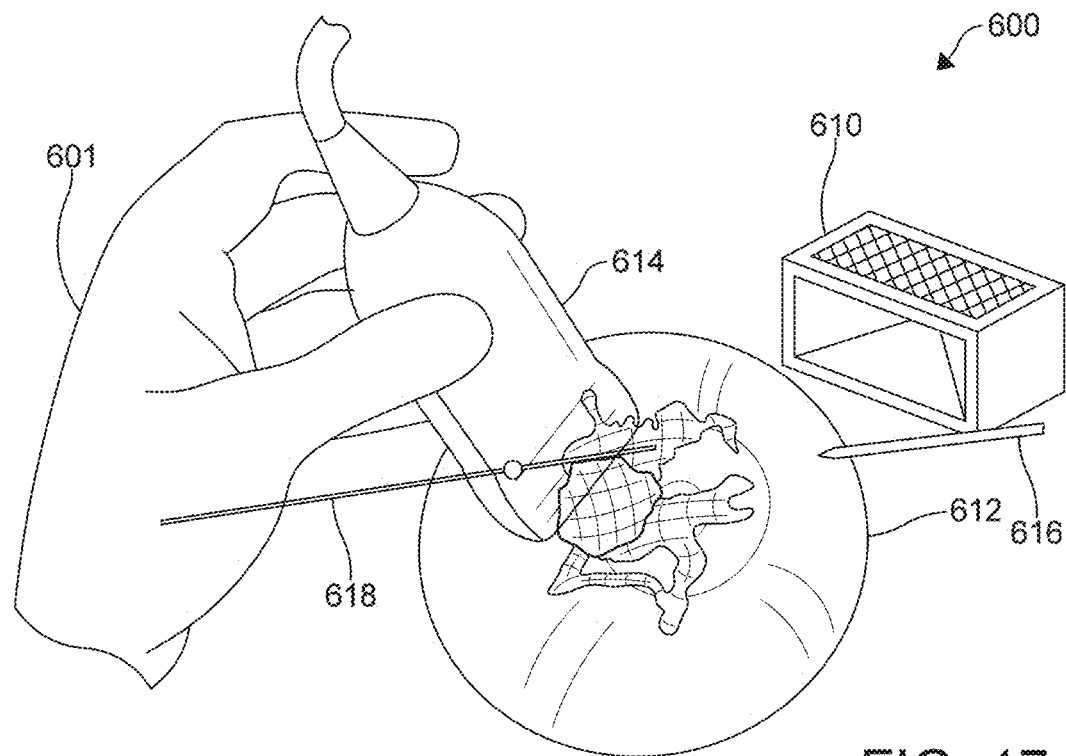
Figure 18:
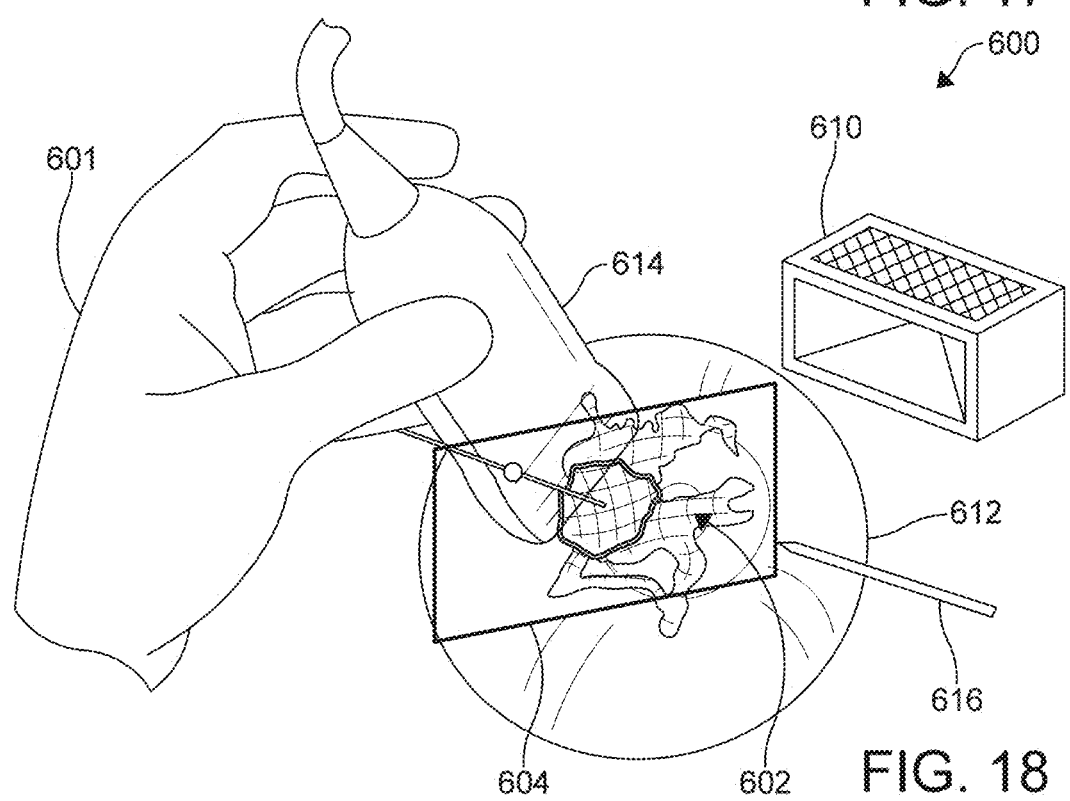
Figure 19:
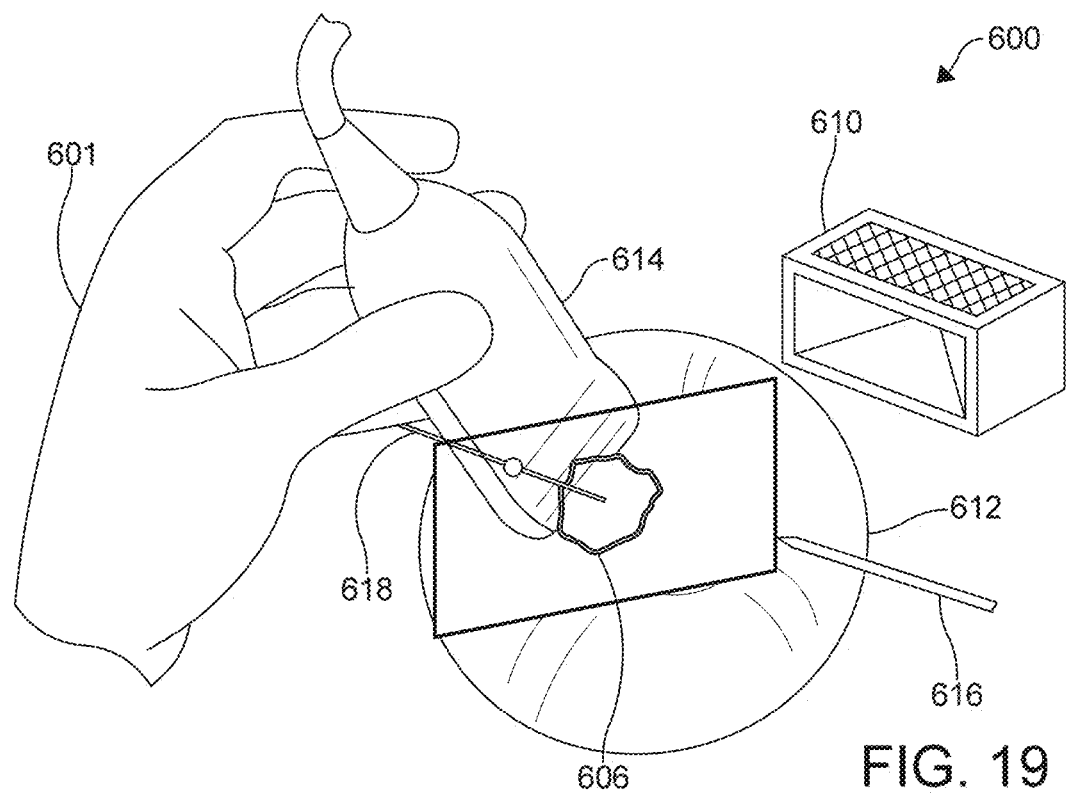
Figure 20:
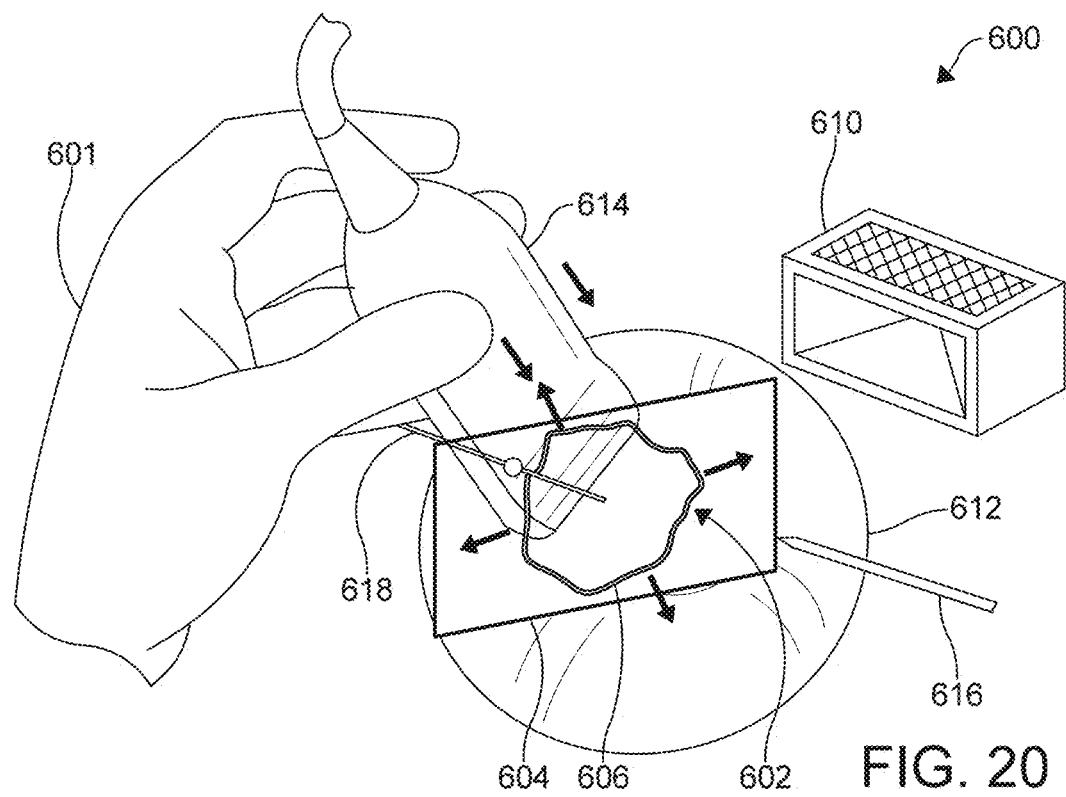

FIG. 15 is schematic view of an exemplary image-guided intervention for the patient involving the intersectional contour of FIG. 13, the exemplary image guided intervention including a real-time two-dimensional sector image of the patient compared with a three-dimensional holographic image of the patient (left), and re-registration of the three-dimensional holographic image of the patient with the two-dimensional sector image of the patient (right);

FIG. 16 is a top perspective view of the exemplary image-guided intervention shown in FIG. 15, from a point of view of an operator of the augmented reality system, and further showing an ultrasound scanning of a portion of a patient with an ultrasound probe and the ultrasound probe being pressed against the patient, and an offset first optical image target for use with the augmented reality system;

FIG. 17 is a top perspective view of the image-guided intervention shown in FIG. 16, and further illustrating a three-dimensional holographic image of the patient from a MDCT scan of the patient, the three-dimensional holographic image showing target tissue for the intervention;

FIG. 18 is a top perspective view of the image-guided intervention shown in FIG. 17, and further illustrating a real-time two-dimensional sector image from the ultrasound scan overlaid with the three-dimensional holographic image of the patient from the MDCT scan;

FIG. 19 is a top perspective view of the image-guided intervention shown in FIG. 18, and further illustrating a generation of an intersectional contour of the target tissue on the ultrasound plane; and FIG. 20 is a top perspective view of the image-guided intervention shown in FIG. 19, and further illustrating a change in shape of the intersectional contour on the real-time two-dimensional sector image with movement of the ultrasound probe.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature unless otherwise disclosed, and thus, the order of the steps can be different in various embodiments, including where certain steps can be simultaneously performed.

I. Definitions

Unless otherwise defined, all technical terms used herein have the same meaning as commonly understood by one of ordinary skill in the art to which the present disclosure pertains.

As used herein, the terms "a" and "an" indicate "at least one" of the item is present; a plurality of such items may be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a process reciting elements A, B and C specifically envisions embodiments consisting of, and consisting essentially of, A, B and C, excluding an element D that may be recited in the art, even though element D is not explicitly described as being excluded herein.

As referred to herein, disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

As used herein, the term "percutaneous" refers to something that is made, done, or effected through the skin.

As used herein, the term "percutaneous medical procedure" refers to accessing the internal organs or tissues via needle-puncture of the skin, rather than by using an open approach where the internal organs or tissues are exposed (typically with a scalpel).

As used herein, the term "non-vascular" when used with "percutaneous medical procedure" refers to a medical procedure performed on any portion of the subject's body distinct from the vasculature that is accessed percutaneously. Examples of percutaneous medical procedures can include a biopsy, a tissue ablation, a cryotherapy procedure, a brachytherapy procedure, an endovascular procedure, a drainage procedure an orthopedic procedure, a pain management procedure, a vertebroplasty procedure, a pedicle/screw placement procedure, a guidewire-placement procedure, a SI-Joint fixation procedure, a training procedure, or the like.

As used herein, the term "interventional device" refers to a medical instrument used during the non-vascular percutaneous medical procedure.

As used herein, the term "tracking system" refers to something used to observe one or more objects undergoing motion and supply a timely ordered sequence of tracking data (e.g., location data, orientation data, or the like) in a tracking coordinate system for further processing. As an example, the tracking system can be an electromagnetic tracking system that can observe an interventional device equipped with a sensor-coil as the interventional device moves through a patient's body.

As used herein, the term "tracking data" refers to information recorded by the tracking system related to an observation of one or more objects undergoing motion.

As used herein, the term "tracking coordinate system" refers to a 3D Cartesian coordinate system that uses one or more numbers to determine the position of points or other geometric elements unique to the particular tracking system. For example, the tracking coordinate system can be rotated, scaled, or the like, from a standard 3D Cartesian coordinate system.

As used herein, the term "head-mounted device" or "headset" or "HMD" refers to a display device, configured to be worn on the head, that has one or more display optics (including lenses) in front of one or more eyes. These terms may be referred to even more generally by the term "augmented reality system." In some instances, the head-mounted device can also include a non-transitory memory and a processing unit. An example of a suitable head-mounted device is a Microsoft HoloLens®.

As used herein, the term "imaging system" or "image acquisition apparatus" or the like refers to technology that creates a visual representation of the interior of a patient's body. For example, the imaging system can be a computed tomography (CT) system, a fluoroscopy system, a magnetic resonance imaging (MRI) system, an ultrasound (US) system, or the like.

As used herein, the terms "coordinate system" or "augmented realty system coordinate system" refers to a 3D Cartesian coordinate system that uses one or more numbers to determine the position of points or other geometric elements unique to the particular augmented reality system or image acquisition apparatus to which it pertains. For example, the headset coordinate system can be rotated, scaled, or the like, from a standard 3D Cartesian coordinate system.

As used herein, the terms "image data" or "image dataset" refers to information recorded in 3D by the imaging system related to an observation of the interior of the patient's body. For example, the "image data" or "image dataset" can include processed two-dimensional or three-dimensional images or models such as tomographic images, e.g., represented by data formatted according to the Digital Imaging and Communications in Medicine (DICOM) standard or other relevant imaging standards.

As used herein, the terms "imaging coordinate system" or "image acquisition apparatus coordinate system" refers to a 3D Cartesian coordinate system that uses one or more numbers to determine the position of points or other geometric elements unique to the particular imaging system. For example, the imaging coordinate system can be rotated, scaled, or the like, from a standard 3D Cartesian coordinate system.

As used herein, the terms "hologram", "holographic," "holographic projection", or "holographic representation" refer to a computer-generated image projected to a lens of a headset. Generally, a hologram can be generated synthetically (in an augmented reality (AR)) and is not related to physical reality.

As used herein, the term "physical" refers to something real. Something that is physical is not holographic (or not computer-generated).

As used herein, the term "two-dimensional" or "2D" refers to something represented in two physical dimensions.

As used herein, the term "three-dimensional" or "3D" refers to something represented in three physical dimensions. An element that is "4D" (e.g., 3D plus a time and/or motion dimension) would be encompassed by the definition of three-dimensional or 3D.

As used herein, the term "integrated" can refer to two things being linked or coordinated. For example, a coil-sensor can be integrated with an interventional device.

As used herein, the term "degrees-of-freedom" or "DOF" refers to a number of independently variable factors. For example, a tracking system can have six degrees-of-freedom (or 6DOF), a 3D point and 3 dimensions of rotation.

As used herein, the term "real-time" refers to the actual time during which a process or event occurs. In other words, a real-time event is done live (within milliseconds so that results are available immediately as feedback). For example, a real-time event can be represented within 100 milliseconds of the event occurring.

As used herein, the terms "subject" and "patient" can be used interchangeably and refer to any vertebrate organism.

II. Pre-Registration

Figure 1:
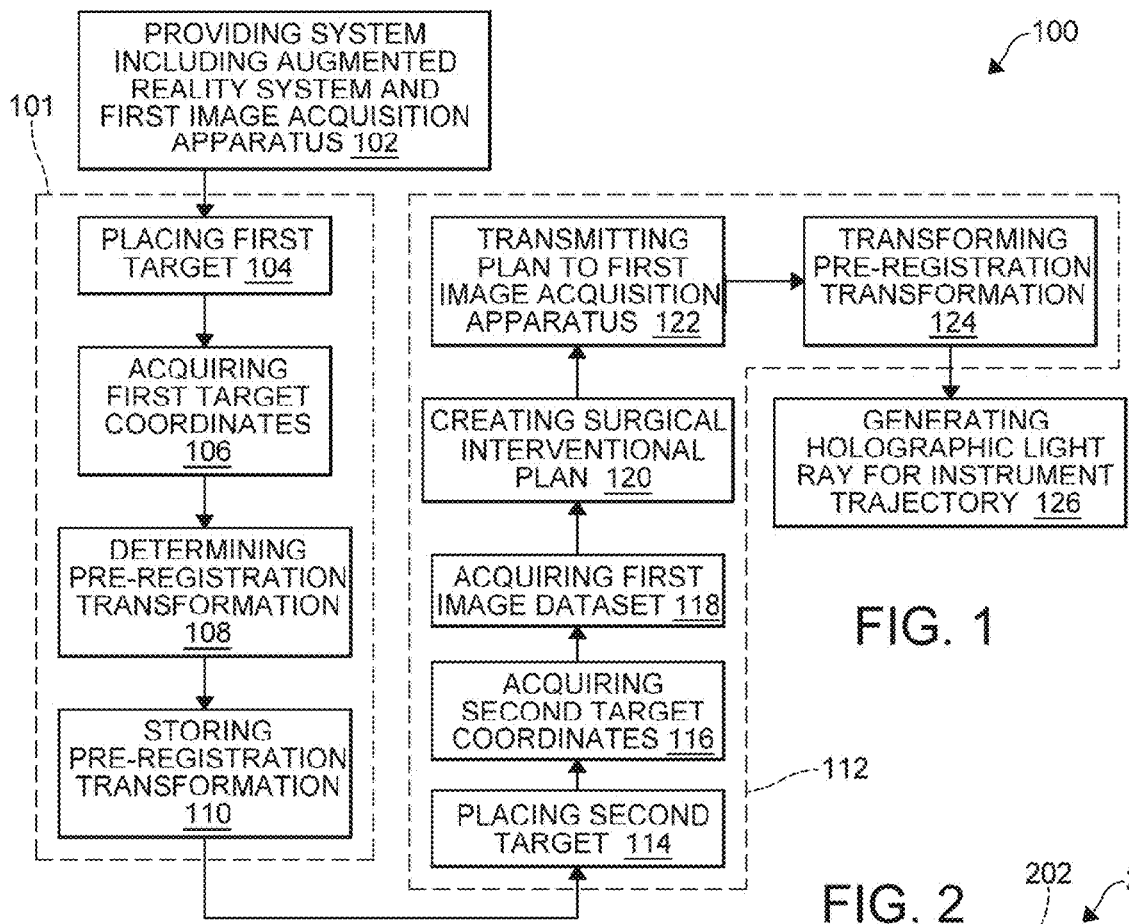
FIG. 1 is a flow diagram illustrating a method for performing a pre-registration associated with an image-guided intervention for a patient, according to one embodiment of the disclosure.
Figure 2:
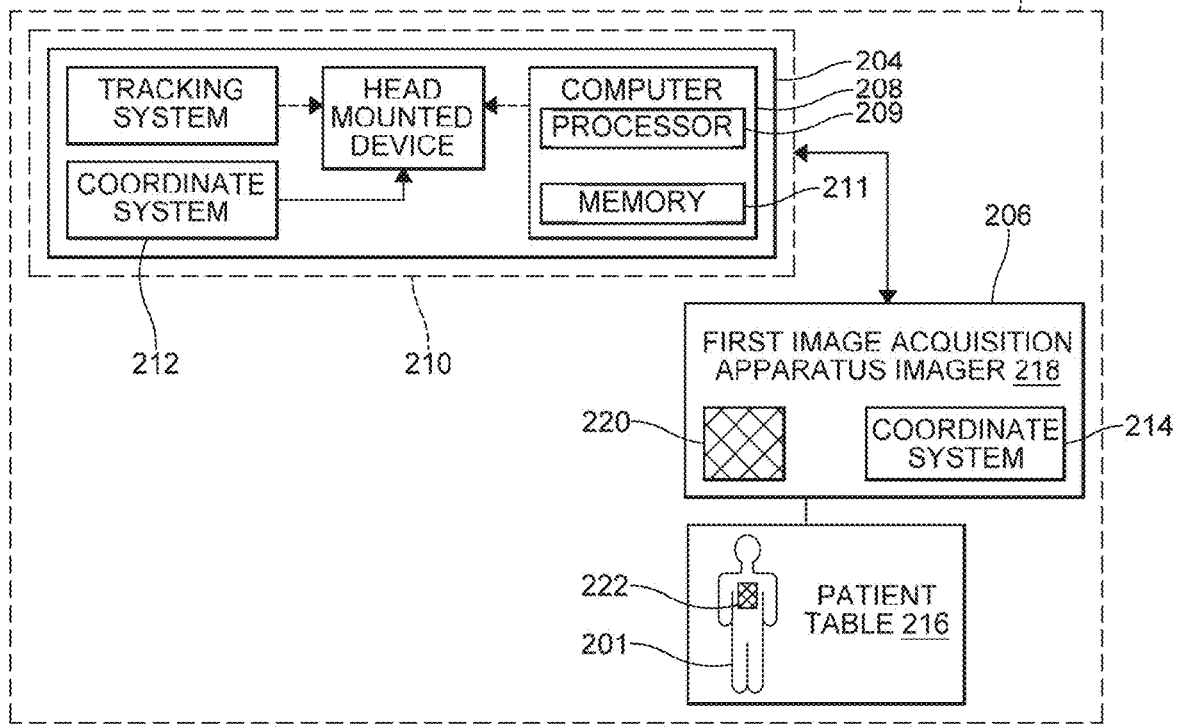
FIG. 2 is a schematic diagram of a system according to one embodiment of the disclosure, the system adapted for use in the pre-registration method of FIG. 1.

FIGS. 1-2 illustrate a method 100 and a system 200 of image-guided intervention involving pre-registration, as described further herein. The method 100 includes a step 102 of providing the system 200, as shown in FIG. 2, for performing the image-guided intervention on a patient 201. The system 200 includes an installation 202 of an augmented reality system 204 at a first image acquisition apparatus 206. The image-guided intervention may be, as one non-limiting example, a percutaneous medical procedure.

Figure 3:
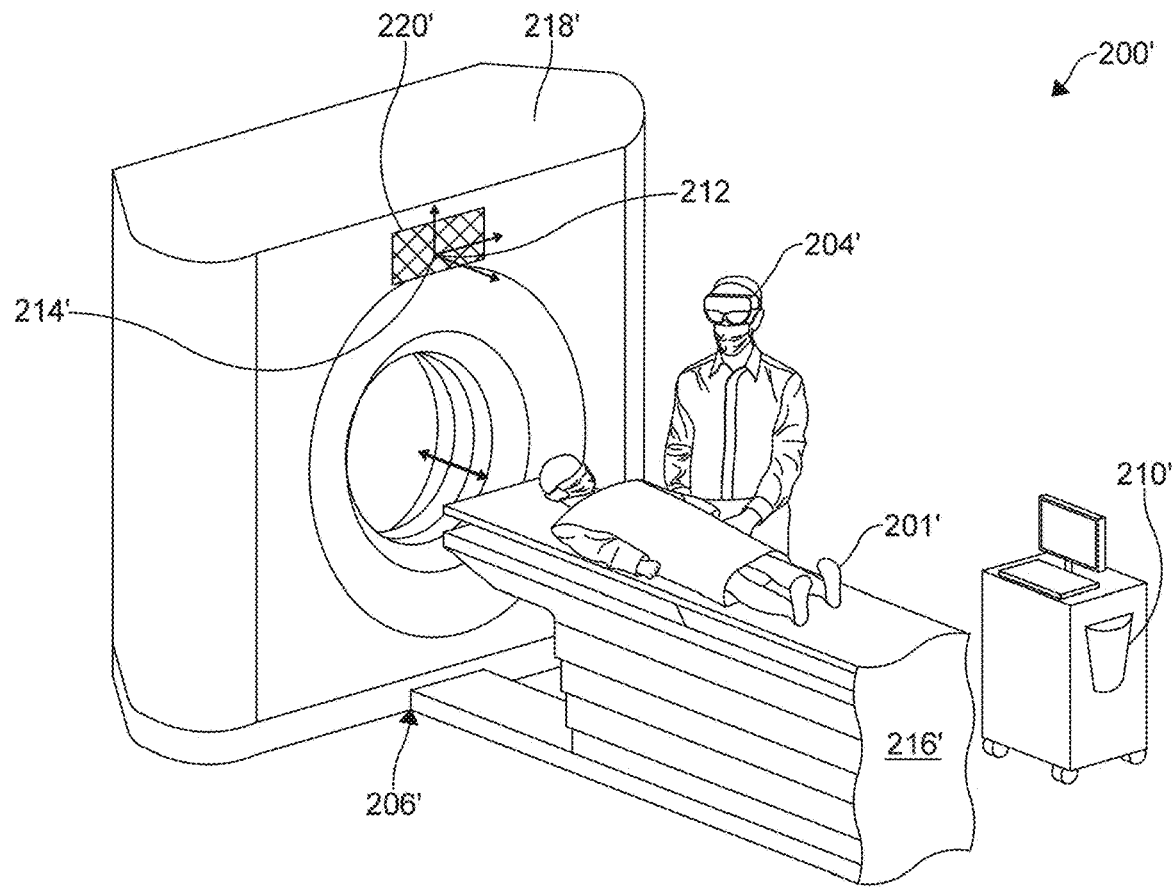
FIG. 3 is a perspective view of an imaging system according to one embodiment of the disclosure and adapted for use with a holographic system and method, the imaging system shown as a multirow detector computerized tomography (MDCT) scanner with associated table.
Figure 4A:
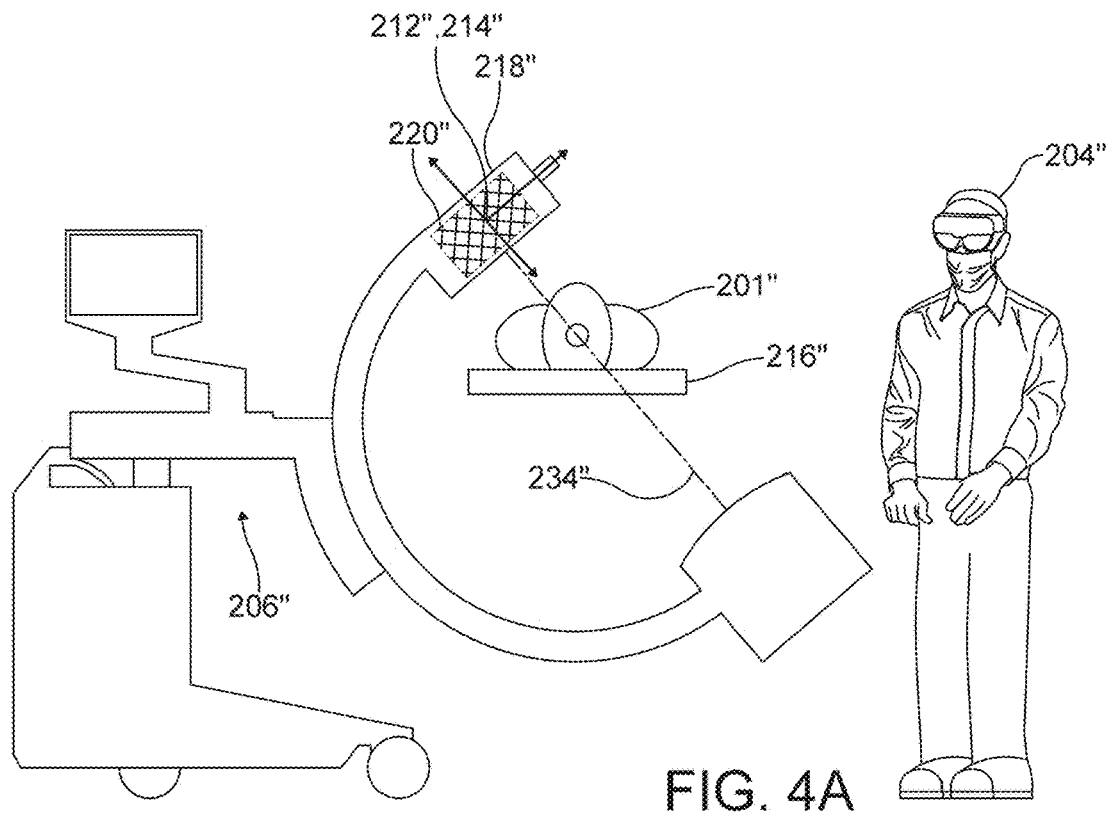
FIG. 4A is a perspective view of an imaging system according to another embodiment of the disclosure and adapted for use with a holographic system and a method, the imaging system shown as a C-arm angiography fluoroscopy unit (Cone beam CT or CBCT) with the X-ray source and detectors mounted on a C-arm apparatus adjacent an associated table.
Figure 4B:
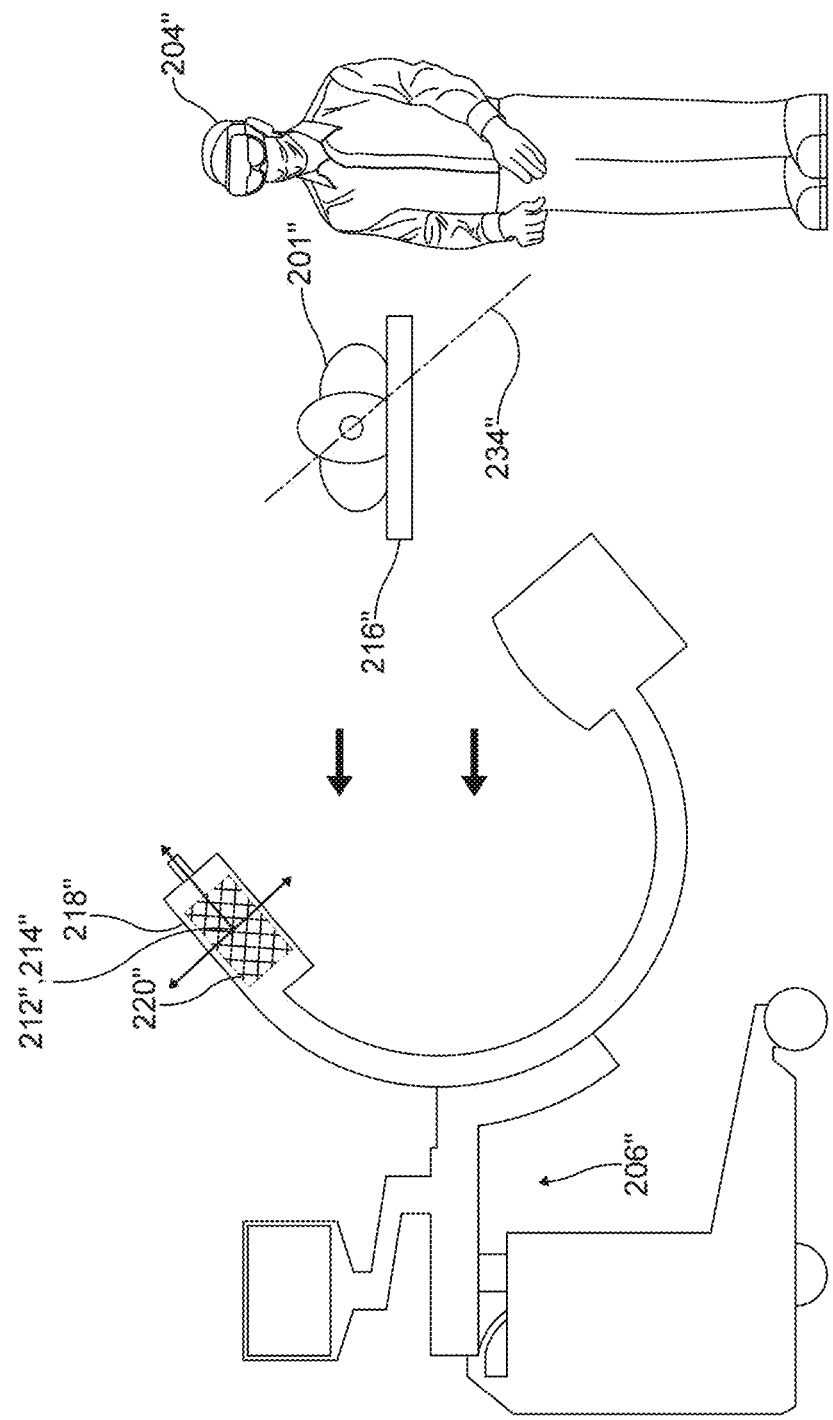
FIG. 4B is a perspective view of the imaging system shown in FIG. 4A, but with the C-arm angiography fluoroscopy unit moved away from the table and a holographic light ray remaining at the table for the operator to use in trajectory planning without interference from the C-arm angiography fluoroscopy unit.

As non-limiting examples, and as illustrated further in FIGS. 3 and 4, the first image acquisition apparatus 206 may be one of a multidetector row computerized tomography (MDCT) imager (shown in FIG. 3) and a C-arm angio fluoroscopy imager (shown in FIGS. 4A and 4B). One of ordinary skill in the art may also select other suitable types of imaging systems for the first image acquisition apparatus 206 within the scope of the present disclosure.

The augmented reality system 204 is in communication with a computer 208 having a processor 209 and a memory 211. The memory 211 may include non-transitory processor-executable instructions directing the augmented reality system 204 to depict a first holographic image dataset adjacent to the patient 201. The first holographic image dataset may define a three-dimensional image volume, for example. The computer 208 may be configured to receive the surgical interventional plan from the first image acquisition apparatus 206.

In a particular embodiment, the augmented reality system 204 may include a stereoscopic head mounted display system such as the Microsoft HoloLens®, with a tracking system (inertial measurement unit), an integrated CPU and holographic processing unit, a camera, and holographic projection lenses. Other suitable types of the augmented reality system 204 may also be selected by a skilled artisan within the scope of the present disclosure.

The augmented reality system 204 may be initially disposed at a predetermined storage position 210 relative to the first imaging acquisition apparatus 206. The augmented reality system 204 may have an augmented reality system coordinate system 212, and the first image acquisition apparatus 206 may have a first image acquisition apparatus coordinate system 214. The augmented reality system coordinate system 212 is different from the first image acquisition apparatus coordinate system 214.

In particular embodiments, the first image acquisition apparatus coordinate system 214 and the augmented reality system coordinate system 212 may be depicted through use of phantom lines with a delineated coordinate axis aligned with imagers, lasers, or phantom lines aligned using imaging results at a fixed patient table position.

The computer 208 is also configured to transform the first image acquisition apparatus coordinate system 214 to the augmented reality system coordinate system 212 for the first holographic image dataset, for example, according to the pre-registration transformation technique of the present disclosure.

The first image acquisition apparatus 206 further has a patient table 216 for receiving the patient 201 and an imager 218 for acquiring a first holographic image dataset from the patient 201 while on the patient table 216.

With further reference to FIGS. 1 and 2, the method 100 further includes an installation step 101. The installation step 101 may include a step 104 of placing a first optical image target 220 at a predetermined location on the imager 218. In particular embodiments, where the predetermined location for the first optical image target 220 is the imager 218, the image-guided intervention for the patient 201 may further includes a step of aligning the imager 218 with the trajectory for the interventional instrument to be used in the image-guided intervention for the patient 201.

In a step 106, first optical image target coordinates are then acquired from the first optical image target 220 with the augmented reality system 204. The step 106 of acquiring the first optical image target coordinates from the first optical image target 220 with the augmented reality system 204 may include moving the augmented reality system 204 so that the first optical image target 220 is in a field-of-view of the augmented reality system 204.

A pre-registration transformation is then determined in a step 108 using the first optical image target coordinates, with the pre-registration transformation being of the first image acquisition apparatus coordinate system 214 into the augmented reality system coordinate system 212. The pre-registration transformation may involve rigid-body affine, as a non-limiting example.

In a step 110, the pre-registration transformation is stored in the memory 211 of the computer 208, whereby a pre-registration of the first image acquisition apparatus 206 with the augmented reality system 204 is performed. It should be understood that the pre-registration may then be re-used for each subsequent patient, and does not need to be performed again unless the system does not verify the accuracy or validity of the pre-registration.

Following the installation step 101 of the augmented reality system 204 and the pre-registration of the first image acquisition apparatus 206 with the augmented reality system 204, the method 100 further includes a step 112 of applying the pre-registration transformation to transform the first holographic image dataset from the first image acquisition apparatus coordinate system 214 to the augmented reality system coordinate system 212.

In particular, the step 112 of applying the pre-registration transformation may occur during the image-guided intervention, which in turn may include a step 114 of placing a second image target 222 on the patient 201 while on the patient table 216. Second optical image target coordinates may then be acquired in a step 116 from the second image target 222 with the augmented reality system 204. In a step 118, a first holographic image dataset of a portion of the patient 201 on the patient table 216 is then acquired.

With the first holographic image dataset acquired, the operator then, in a step 120, creates a surgical interventional plan using the first image acquisition apparatus 206, for example, using hardware and software of the first image acquisition apparatus 206. The surgical interventional plan including a delineation of target tissue in the first holographic image dataset, for example, the identification of the target tissue in a three-dimensional holographic image or model derived from the first holographic image dataset. It should be appreciated that the surgical interventional plan is likewise provided in the first image acquisition apparatus coordinate system 214.

In a step 122, the surgical interventional plan is then transmitted from the first image acquisition apparatus 206 to the augmented reality system 204. Upon being transmitted in step 122, the surgical interventional plan in then transformed in a step 124 from a first image acquisition apparatus coordinate system 214 of the first image acquisition apparatus into the augmented reality system coordinate system 212 using the pre-registration transformation from the installation step 101. Subsequently, the augmented reality system 204 may be used in a step 126 to generate a holographic light ray (shown in FIGS. 4A and 4B, for example) to show the operator a trajectory for the interventional instrument according to the surgical interventional plan, for use in the image-guided intervention.

It should be appreciated that, in certain embodiments, such as in the case of a multi-detector row CT scanner, the patient table 216 is translatable or movable. In this case, the method 100 may further include at least one of the following steps: i) determining and registering a position of the patient table 216 with the augmented reality system 204; ii) placing an additional image target (not shown) at the patient table 216, and acquiring an additional image target dataset from the additional image target with the augmented reality system 204, and determining a position of the patient table 216 by the augmented reality system 204 based on the additional image target dataset; and iii) transmitting a position of the patient table 216 from a patient table sensor (shown as "217" in FIG. 6) on the patient table 216 to the augmented reality system 204. Other suitable means for providing relevant information on the position of the patient table 216 to the augmented reality system 204, for use in creating the pre-registration transformation, may also be employed within the scope of the present disclosure.

Example Pre-Registration Techniques:

1. Summary

With reference to FIGS. 3 and 5-6, and FIGS. 4 and 7-8, further exemplary embodiments associated with the pre-registration techniques described hereinabove are shown and explained. Like or related structure in FIGS. 3 and 5-6, in comparison to that shown in FIGS. 1-2, are reproduced in FIGS. 3 and 5-6 with a same reference number and a prime (') symbol for purpose of clarity. Like or related structure in FIGS. 4A-4B and 7-8, in comparison to that shown in FIGS. 1-2, are reproduced in FIGS. 4A-4B and 7-8 with a same reference number and a prime (') symbol for purpose of clarity.

In particular embodiments, as illustrated in FIGS. 3-8, a minimally-invasive surgical intervention may be planned in the system 200', 200" where the first image acquisition apparatus 206', 206" is tomographic imaging system such as a multi-detector row CT (MDCT, shown in FIGS. 3 and 5-6) or a C-arm angio fluoroscopy imager (shown in FIGS. 4A-4B and 7-8), as described further herein. The system 200', 200" may further include the augmented realty system 204', 204" in the form of a head mounted display (HMD) such as a Microsoft HoloLens® including the computer 208', 208" with the associated processor 209', 209" and the memory 211', 211". The system 200', 200" may also include the predetermined storage position 210', 210" in the form of an HMD docking station or storage pod disposed adjacent to the first image acquisition apparatus 206', 206", a table position sensor transmitter 217' (in the case of the MDCT) or an alert module for table movement 219" (in the case of the C-arm angio fluoroscopy imager), and the first optical image target 220', 220" (only during the installation step 101', 101"). The patient table sensor 217' or the alert module 219" may be configured for detecting a position of the patient table 216', 216" and for transmitting to the augmented reality system 204', 204" the position of the patient table 216', 216", in operation.

The system 200', 200" further may include a computer 224', 224" associated with the MDCT or a C-arm angio fluoroscopy imager. The computer 224', 224" may have a computer display 226', 226" and a cursor controller 228', 228" configured to allow the operator to plan for the trajectory of a surgical instrument during the procedure. To facilitate the planning, and as further shown in FIGS. 5 and 7, the system 200', 200" may also include a plan interventional instrument 230', 230" that is configured to permit the user to create a surgical interventional plan and to store the surgical interventional plan on a memory of the computer 224', 224" of first image acquisition apparatus 206', 206" (such as the MDCT or the C-arm angio fluoroscopy imager). In this case, it should be appreciated that the surgical interventional plan may include a delineation of target tissue in the first holographic image dataset and digital content representing a path of the surgical instrument to the target tissue.

Figure 5:
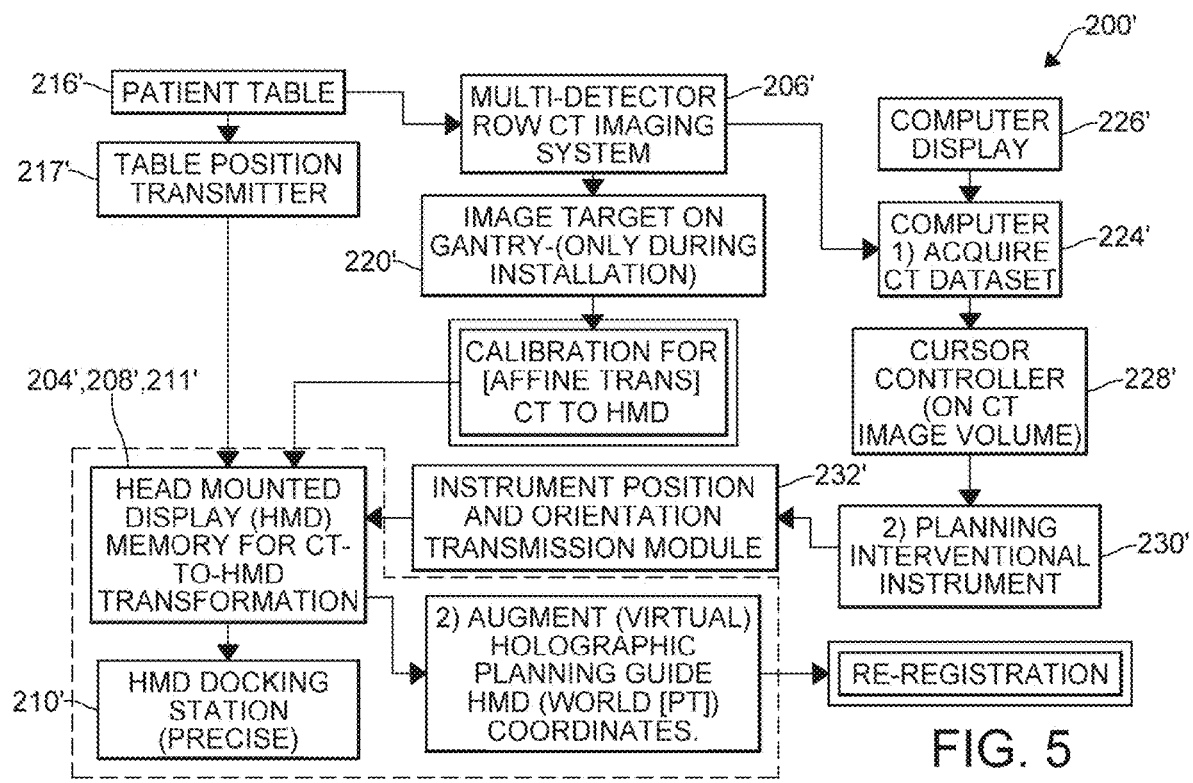
FIG. 5 is a schematic diagram showing use of the multirow detector computerized tomography (CT) scanner shown in FIG. 3 with the method and the system shown in FIGS. 1 and 2.

With continued reference to just FIG. 5, the first image acquisition apparatus 206' or MDCT may further have an instrument position and orientation transmission module 232' configured to transmit the surgical interventional plan from the plan interventional instrument 230' to the augmented reality system 204'.

It should be understood that the interventional plan of the present disclosure has digital (i.e., virtual) content representing a path of a surgical instrument to the target tissue or anatomical structures, which may be visually represented as surfaces (e.g., point cloud or vertices) by the augmented reality system 204', 204". The digital treatment or interventional plan can be specified, for example, by selecting a 3D point on the target tissue and drawing a line on the anatomical image representing a desired path avoiding critical structures.

In particular, the plan may be transmitted to the augmented reality system 204', 204" in the form of an Augmented/Extended Reality (AR) headset, for example, also referred to as a head mounted display (HMD) or a suitable device with similar capabilities. Prior to transmission, i.e., at the time of installation, the pre-registration may be performed so that the plan is transformed to coordinates of the HMD. This enables the virtual representation of the planned trajectory, for example, as a holographic light ray (HLR), and target tissue to be augmented on to the real patient as a holographic content in the HMD (world) coordinates. In turn, this allows the operator to align a physical instrument such as a medical probe for treatment and/or diagnosis. Live imaging acquired from the imaging system can then be used to re-register, as described further hereinbelow, the treatment plan including digital structures derived from a 3D dataset and instrument trajectories for improved alignment to the target.

2. Pre-Registration of 3D Planning Data into HMD Coordinates

Figure 6:
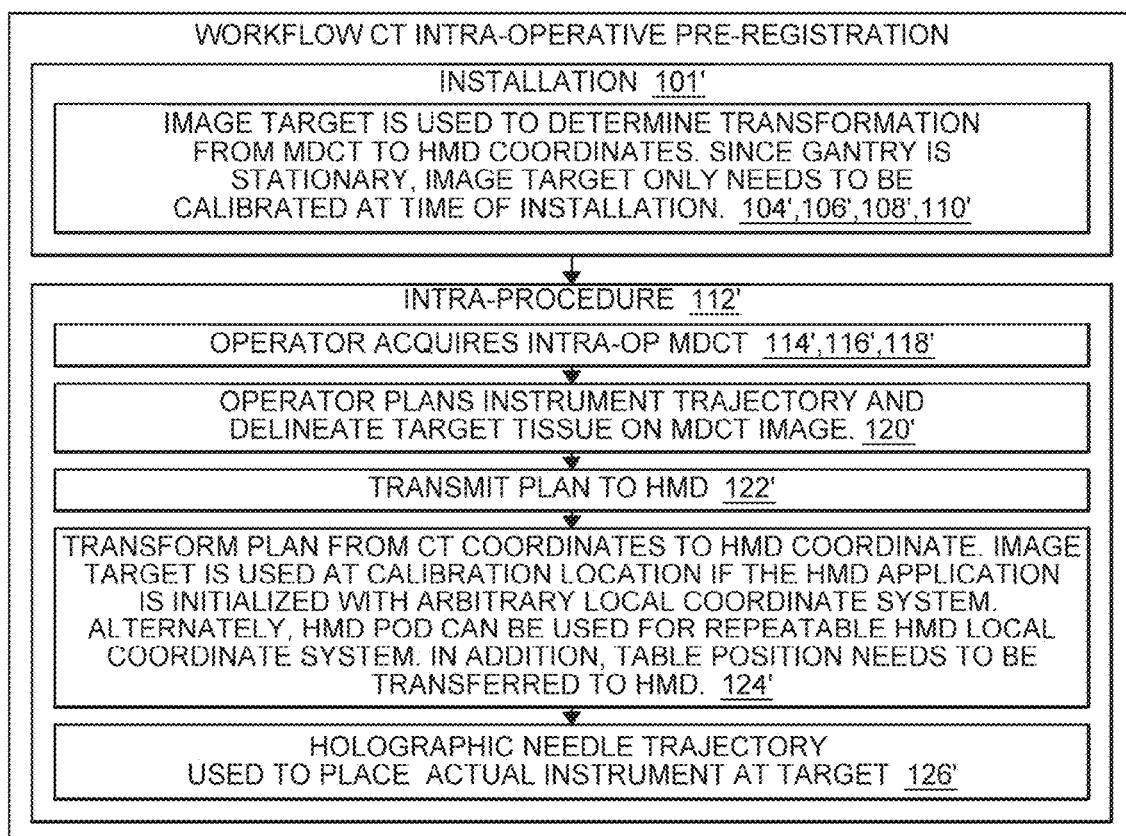
FIG. 6 is a flowchart illustrating a method or workflow for intra-operative pre-registration of the imaging system shown in FIG. 5 to a coordinate system of a head mounted display of the holographic system.
Figure 8:
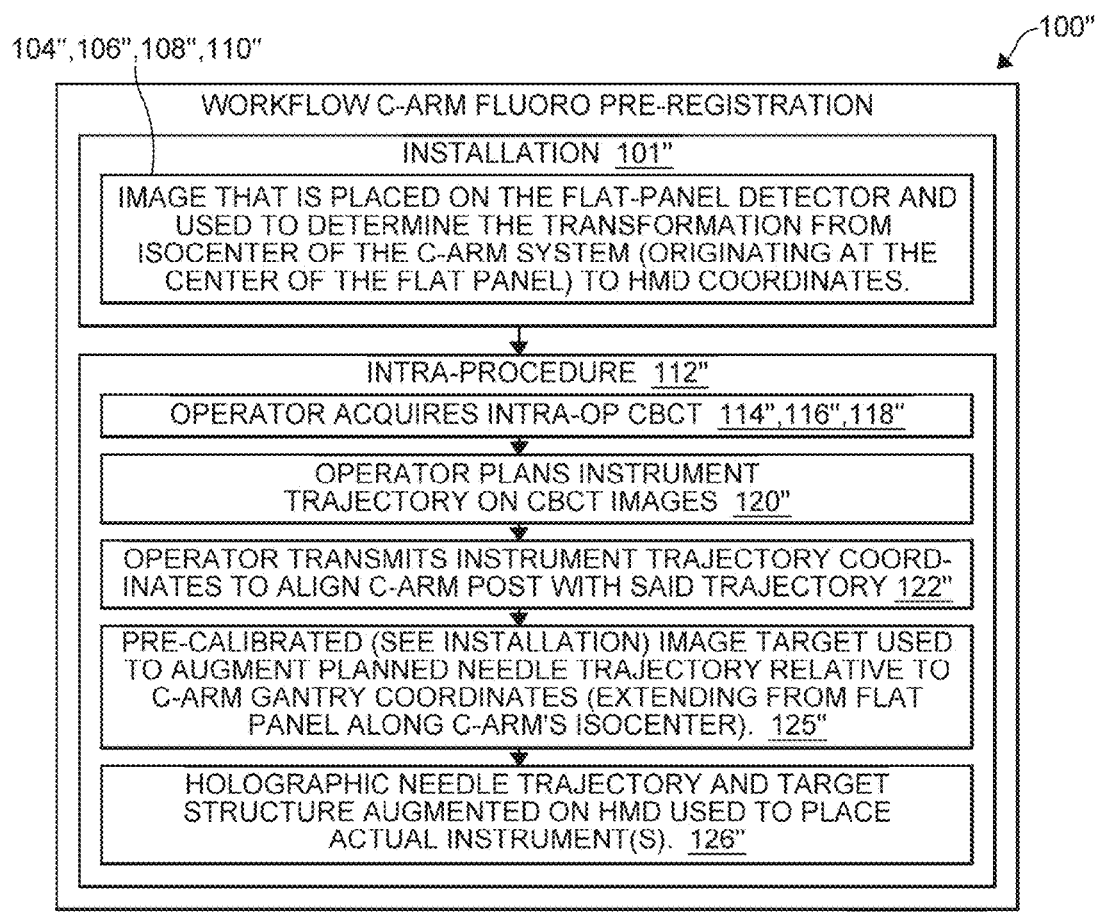
FIG. 8 is a flowchart illustrating a method or workflow for intra-operative pre-registration of the imaging system shown in FIGS. 4A and 4B to a coordinate system of a head mounted display of the holographic system.

Prior to the first use of the augmented reality system 204', 204" or HMD in combination with the system 200', 200", the HMD may pre-registered by integration with the system 200', 200" in accordance with the method 100', 100" as further shown in FIGS. 6 and 8 relative to the specific examples of the MDCT and C-arm angio fluoroscopy unit, respectively. This step is performed once at the time of the installation step 101', 101", so that the interventional plan can be automatically transformed from imaging by the first image acquisition apparatus 206', 206" to HMD coordinates leading to registration and augmented with and on to the patient 201', 201". More generally, the pre-registration method is not limited to use with pre- or intra-procedure treatment plans but can also be used to register a holographic navigation, i.e., tracked devices system with the system 200', 200".

It should be appreciated that the pre-registration method enables the HMD to transform treatment planning data from imaging system to HMD (world) coordinates without the need for the operator to perform registration steps during the procedure. Although the pre-registration method 100' is described in FIGS. 3 and 5-6 for the multi-detector row CT (MDCT) imaging system, and the pre-registration method 100" is described in FIGS. 4A-4B and 7-8 for the C-arm angio fluoroscopy unit, it should also be understood that the methods are generally applicable to any 3D imaging system.

The digital treatment or surgical intervention plans can include the position and trajectory ("planned trajectory") of one or a plurality of interventional instruments, including points, linear and curved paths, as well as 3D coordinates representing structures in the operative site as surfaces derived from 3D data set acquired with the imaging system.

A. Multi-Detector Row CT (MDCT) Embodiment

For the multi-detector row CT (MDCT) embodiment shown in FIGS. 3 and 5-6, the first optical image target 220' is placed on the imager 218' such as an imaging systems gantry of the MDCT with a line-of-sight to the HMD. The first optical image target 220' is used to determine a 3D rigid affine transformation from the imager (MDCT) spatial 3D coordinates to holographic coordinates for all future patients. Although not depicted in FIGS. 3 and 5-6, it should be appreciated that an additional image target can also be placed near the skin surface of the patient 201' so that upon detection of the HMD the HLR can terminate at the skin surface representing the percutaneous access location.

In the case of the MDCT gantry, which remains stationary, as shown in FIGS. 5 and 6, the HMD can be calibrated with the CT gantry's coordinate system, for example, [x,y] origin at an aperture isocenter, z-axis along patient table. In this case, the trajectory planned on the CT console may then be transmitted to the HMD to augment the HLR in patient coordinates, for example, as shown in FIG. 6. A guide for advancing the intervention instrument, as described herein, is thereby provided. The HMD can also receive data to compensate for the movable CT table position reported on the gantry display.

In particular embodiments, as shown in FIGS. 3 and 6, the (x,y) origin of CT coordinates ascribed to the CT reconstructed images can be related to the isocenter of the gantry or imager 218'. The MDCT gantry may not have capability for tilting, which is common for CTs manufactured in recent years. The first optical image target 220' such as a Vuforia® target, commercially available from PTC Inc. in Needham, Massachusetts, or a similarly suitable image target, may be mounted in a precise, repeatable location of the MDCT gantry and may therefore be used to determine the transformation from MDCT to HMD coordinates. This calibration or integration is performed at the time of installation, and not by the end-operator for each case, and then stored by the HMD. Advantageously, this enables the operator to use the HMD, and said pre-registration transformation, without the need for the registration steps at the time of the image-guided intervention which would otherwise lead to inefficient workflow.

For use by the operator, a virtual needle or other interventional instrument and delineation of target tissue may be planned on the reconstructed MDCT images in the MDCT coordinates. These 3D coordinates, for example, start [x,y,z] and end point [x,y,z] of the instrument, and target structures represented as surfaces are transferred to the augmented reality system 204' or HMD. The MDCT table position may also be sent to the HMD at this time.

After planning the virtual instrument on the MDCT display, the operator may then retrieve the HMD from the predetermined storage position 210' such as a storage pod, which is associated with a repeatable "home" position. The HMD then applies the MDCT-to-HMD pre-registration transformation to the virtual instrument and target structure coordinates to project the holographic interventional instrument or needle in the HMD (world) coordinates, so that it can be used as a guide for the interventional procedure.

B. C-Arm Angiography Fluoroscopy Unit (Cone Beam CT or CBCT) Embodiment:

For the C-arm Angiography Fluoroscopy Unit embodiment shown in FIGS. 4A-4B and 7-8, the first optical image target 220" is placed on the imager 218" such as a flat panel detector of the C-arm with a line-of-sight to the HMD. The first optical image target 220" is used to determine a transformation from the isocenter of the C-arm system (e.g., originating at a center of the flat panel) to holographic coordinates of the HMD for all future patients. Although not depicted in FIGS. 4A-4B and 7-8, it should be appreciated that an additional image target can also be placed near the skin surface of the patient 201" so that upon detection of the HMD the HLR can terminate at the skin surface representing the percutaneous access location.

Figure 7:
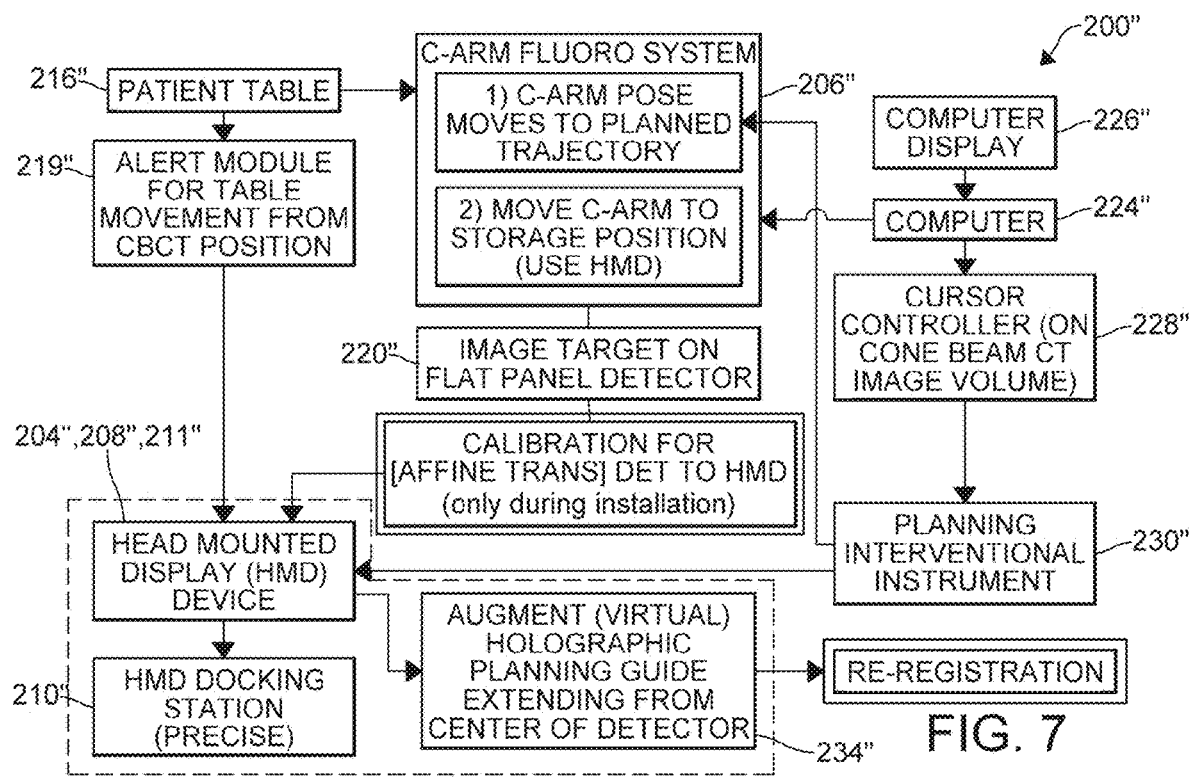
FIG. 7 is a schematic diagram showing use of the C-arm angiography fluoroscopy unit shown in FIGS. 4A and 4B with the method and system shown in FIGS. 1 and 2.

In a particular example, the first optical image target 220" may be a Vuforia® image target or similar optical target. The first optical image target 220" is mounted in a precise, repeatable location on the flat panel detector of the C-arm used to determine the transformation from an isocenter of the C-arm system, i.e., originating at the center of the flat panel, to the augmented reality system 204" or HMD coordinates. As with the MDCT embodiment shown in FIGS. 3 and 5-6, this calibration or integration is performed at the time of installation, and not by the end-operator, and is stored by the HMD, for example, as shown in FIGS. 7 and 8. This enables the operator to use the augmented reality system 204" in the form of the HMD and the first image acquisition apparatus 206" in the form of the C-arm with the pre-registration for the image-guided intervention and without the need for additional registration steps which would otherwise lead to inefficient workflow.

In yet another example, for use by the operator, the optical image target 220" may be placed on the C-arm detector in a predetermined or designated location, e.g., where a calibration was performed, in order to track its pose. A virtual needle or other interventional instrument may then be planned on the reconstructed Cone Beam CT images in the coordinate system 214" of C-arm Angiography Fluoroscopy Unit, as illustrated in FIG. 4A and shown in step 125" in FIG. 8. These 3D coordinates, for example, start (x,y,z) and end points (x,y,z) of the instrument, may then be sent or transferred to the C-arm system. The C-arm gantry then aligns with the planned trajectory.

It should be appreciated that, although the detector's laser could be used to show the trajectory, a presence of the C-arm can in fact interfere with the access of interventionalist or operator to the patient. Thus, the HMD may further use the first optical image target 220" to locate the C-arm pose. After calibration of the flat panel detector into the HMD coordinates, the first optical image target 220" may be used to locate a holographic light ray (HLR) guide 234" in alignment with the isocenter of C-arm gantry (shown in arbitrary location in FIGS. 4A and 4B). More specifically, the system may apply the memory stored C-arm-to-HMD transformation and the virtual instrument coordinates to project the holographic needle and/or instrument and target structures in HMD (world) coordinates so that the HMD may generate the holographic light ray (HLR) guide 234", as shown in FIGS. 4A and 4B. The C-arm may then be moved away, as shown in FIG. 4B, with the HLR guide 234" remaining. Advantageously, the ability to move the C-arm but retain the HLR guide 234" provides sufficient clearance for implementation of the procedure.

With respect to FIGS. 4A and 4B, an image tracker target is attached and calibrated to the C-arm flat panel detector. After calibration of the flat panel detector into the HMD coordinates, the image tracker target is used to locate a holographic light ray (violet line) in alignment with the isocenter of C-arm gantry (shown in arbitrary location). The operator can then provide a voice command such as "place" that keeps the HLR stationary after the C-arm is moved away to provide sufficient space the interventionalist or operator to position the physical interventional instrument.

III. Re-Registration

Figure 9:
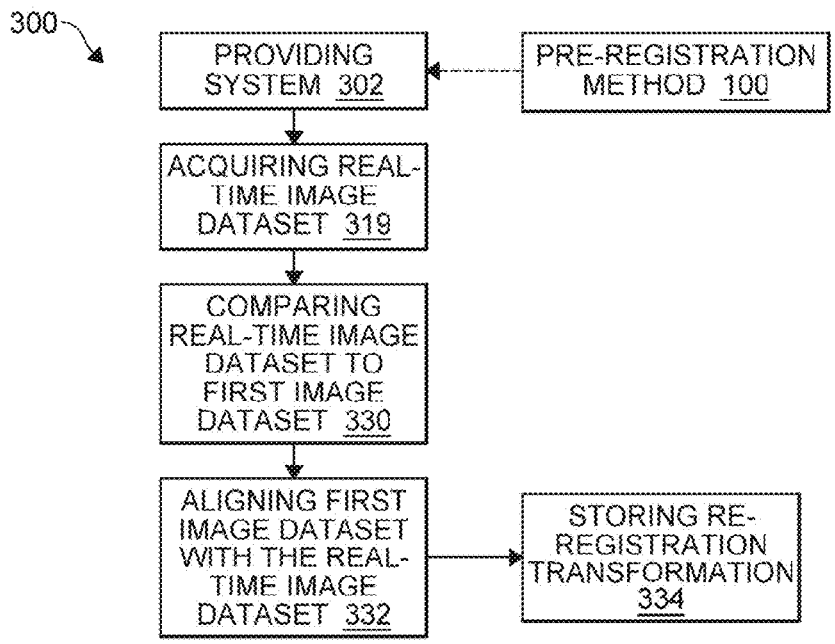
FIG. 9 is a flow diagram illustrating a method for performing a re-registration associated with an image-guided intervention for a patient, according to another embodiment of the disclosure.
Figure 10:
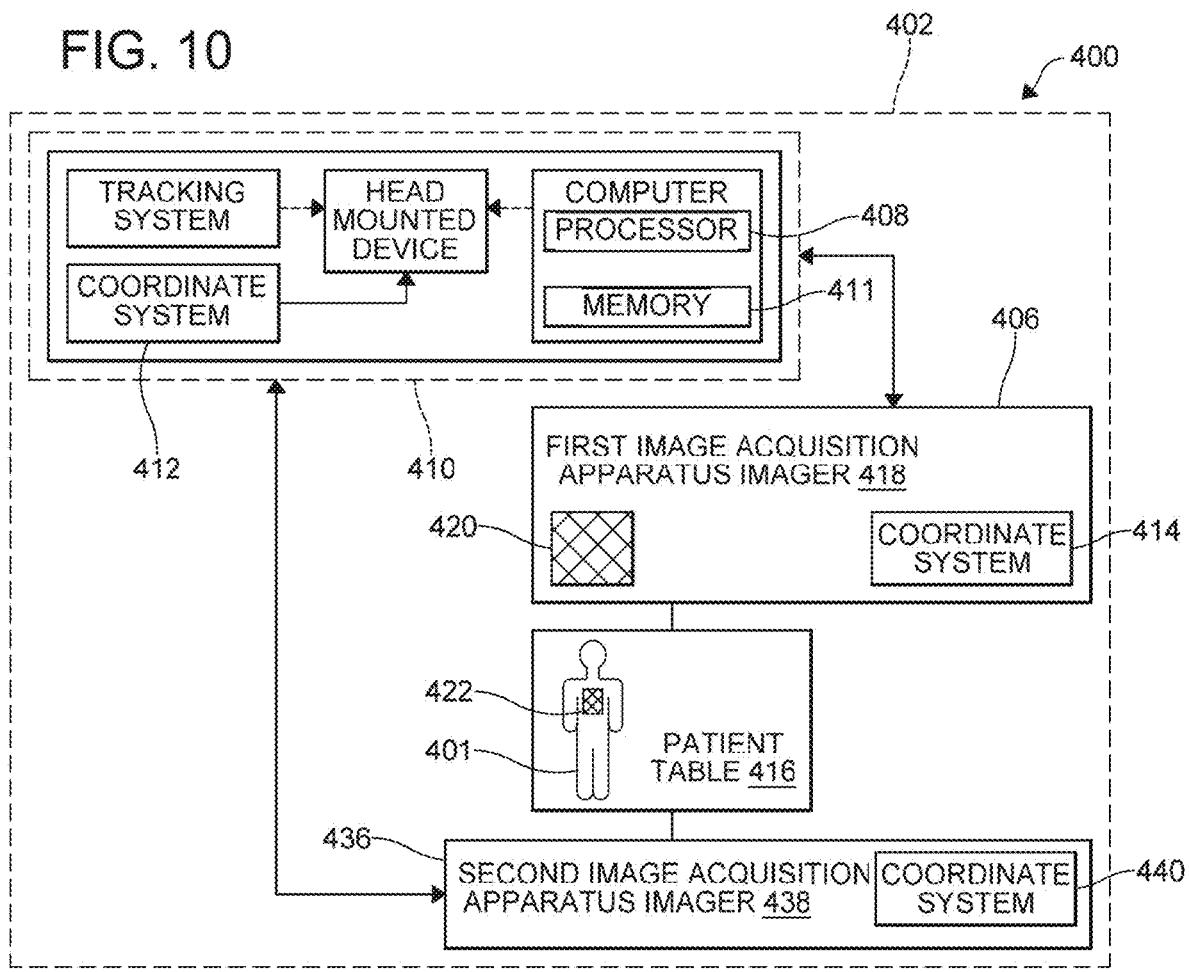
FIG. 10 is a schematic diagram of a system according to another embodiment of the disclosure, the system adapted for use in the re-registration method of FIG. 9.

FIGS. 9-10 illustrate a method 300 and a system 400 of image-guided intervention involving re-registration, as described further herein. Like or related steps or structure from FIGS. 1-2 are shown in FIGS. 9-10 with the same reference number but in a 300- or 400-series, for purpose of clarity.

In particular embodiments, the method 300 and the system 400 involving re-registration may be used in conjunction with the method 100 and the system 200 involving pre-registration, as described hereinabove. However, it should be appreciated that the re-registration method 300 and the system 400 may also be used independently from the pre-registration techniques of the present disclosure, as desired.

The method 300 includes a step 302 of providing the system 400, as shown in FIG. 10, for performing the image-guided intervention on a patient 401 including an installation 402 of an augmented reality system 404 at a first image acquisition apparatus 406. As non-limiting examples, the first image acquisition apparatus 406 may be one of a multidetector row computerized tomography (MDCT) imager and a C-arm angio fluoroscopy imager. One of ordinary skill in the art may also select other suitable types of imagers for the first image acquisition apparatus 406 within the scope of the present disclosure.

The augmented reality system 404 is in communication with a computer 408 having a processor 409 and a memory 411. The memory 411 may include non-transitory processor-executable instructions directing the augmented reality system 404 to depict the first holographic image dataset adjacent to the patient 401. The computer 408 may be configured to receive the surgical interventional plan from the first image acquisition apparatus 406.

The augmented reality system 404 may be initially disposed at a predetermined storage position 410 relative to the first image acquisition apparatus 406. The augmented reality system 404 has an augmented reality system coordinate system 412, and the first image acquisition apparatus 406 has a first image acquisition apparatus coordinate system 414. The augmented reality system coordinate system 412 is different from the first image acquisition apparatus coordinate system 414.

In certain examples, the computer 408 may also be configured to transform the first image acquisition apparatus coordinate system 414 to the augmented reality system coordinate system 412 for the first holographic image dataset according to the pre-registration transformation technique, as described hereinabove.

With respect to the re-registration technique described herein, the computer 408 may have an initial transformation of the first image acquisition apparatus coordinate system 414 into the augmented reality system coordinate system 412 stored in the memory of the computer 408. For example, the initial transformation may be the pre-registration transformation as described hereinabove; however, one skilled in the art should appreciate the initial transformation may be provided by other means and is not necessarily the pre-registration transformation.

The first image acquisition apparatus 406 further has a patient table 416 for receiving the patient 401 and an imager 418 for acquiring a first holographic image dataset from the patient 401 while on the patient table 416.

With further reference to FIG. 10, the system 400 further includes a second image acquisition apparatus 436 configured to acquire a real-time holographic image of the patient 401 during an image-guided intervention. The second image acquisition apparatus 436 has an imager 438 and a second image acquisition apparatus coordinate system 440. As a nonlimiting example, the second image acquisition apparatus 436 may be an ultrasound transducer and the imager 438 may be a probe of the ultrasound transducer. One of ordinary skill in the art may also select other suitable imaging systems for the second image acquisition apparatus 436 within the scope of the present disclosure.

With renewed reference to FIG. 9, the method 300 further include a step 319 of acquiring with one of the first image acquisition apparatus 406 and the second image acquisition apparatus 436 a real-time holographic image dataset of the patient 401 during the image-guided intervention. The real-time holographic image dataset may define a two-dimensional planar sector, for example. The real-time holographic image dataset may then be compared in a step 330 with either a position of the patient 401 (e.g., by a simple visual comparison performed by the operator of the augmented reality system 404) or the first holographic image dataset (e.g., by an automated or semi-automated process performed by a computer of the system 200). In a step 332, the first holographic image dataset may then be aligned with the real-time holographic image dataset from the patient to provide a re-registration transformation. The re-registration transformation may then be stored, in a step 334, in the memory 411 of the computer 408 of the augmented reality system 404.

In certain examples, the initial transformation prior to the re-registration technique maybe be the pre-registration transformation, as described hereinabove. In such case, the initial transformation may be determined by the method 100 (shown in FIG. 1) including i) a step 104 of placing a first optical image target 420 at the predetermined location on the imager 418 of the first image acquisition apparatus 406, ii) a step 106 of acquiring first optical image target coordinates from the first optical image target 420 with the augmented reality system 404, and iii) a step 108 of determining the initial transformation as the pre-registration transformation of the first image acquisition apparatus coordinate system 412 into the augmented reality system coordinate system 414 using the first optical image target coordinates.

With renewed reference to FIGS. 9 and 10, the second image acquisition apparatus 436 configured to acquire the real-time holographic image dataset of the patient 401 during the image-guided intervention may be used in the step 319 of acquiring the real-time holographic image dataset of the patient 401 with the second image acquisition apparatus 436. Advantageously, where the first image acquisition apparatus 406 is one of a multidetector row computerized tomography (MDCT) imager and a C-arm angio fluoroscopy imager, and the second image acquisition apparatus is an ultrasound transducer, the employment of the ultrasound transducer for acquiring the real-time holographic image dataset may help minimize radiation exposure to the patient 401.

Where the second image acquisition apparatus 436 is the same as the first image acquisition apparatus 406, such as the MDCT or C-arm angio fluoroscopy imager, it should be appreciated that the system may further include a module with an algorithm used to automatically segment the MDCT to form a surface, plane, or sector in real-time. A skilled artisan may select a suitable algorithm for automatically segmenting the images for this purpose, as desired.

Example Re-Registration Techniques:

With reference to FIGS. 9-12, further exemplary embodiments associated with the re-registration techniques described hereinabove are shown and explained.

1. Re-registration to Account for Movement of Target Tissue:

The re-registration method 300, as described hereinabove, can be used to compensate the initial registration, such as the pre-registration according to the method 100, for motion of the patient 401. The motion may be either gross or physiological motion, for example. The re-registration method 300 uses live imaging from the same or another imaging system to update and improve the registration of the treatment plan to the augmented reality system 404 or HMD coordinates prior to performance of the procedure.

Although live images have a limited field-of-view (FOV), and 3D tomographic imaging does not reflect breathing motion, their combination according to the present disclosure may be used to improve the accuracy of initial registration, and this correction for inaccuracy is generally referred to herein as "re-registration." Live imaging may be used to update the transformation of the target tissue (and other structures derived from the static 3D data set) and the associated planned trajectory to increase the accuracy when implementing the treatment plan.

Spatial registration methods, including the pre-registration method 100 described hereinabove, will transform 3D spatial coordinate datasets such as planned interventional trajectories and anatomical targets based on pre- or intra-procedural 3D data set. For example, such methods may use rigid-body affine matrices to transform (i.e., rotate and translate) the 3D coordinate data into the HMD (or world) coordinates. In contrast, the live imaging such as CT, fluoroscopy, or sonography techniques can reflect motion and deformation but can have the limited field-of-view (e.g., single plane or projection as shown in FIG. 11).

The re-registration method 300 is not limited to use with the pre-registration method or, more generally, is not limited to use with an interventional treatment plan. The re-registration method 300 can be used to update any initial or preliminary registration (such as manual or fiducial marker methods) between live imaging and static 3D imaging data including inter- and intra-modality combinations thereof, for example, between live sonography (two spatial dimensions and time), and segmented 3D (three spatial dimensions) multi-detector row CT data.

Figure 11:
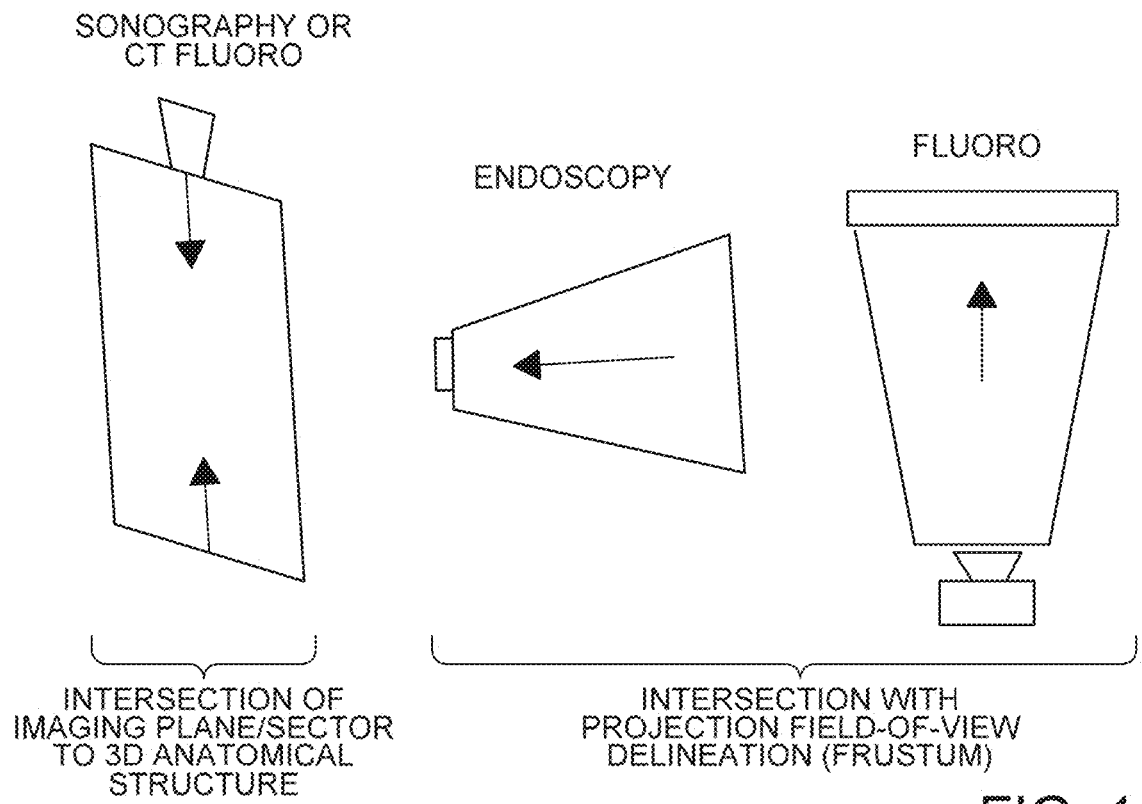
FIG. 11 is a schematic diagram showing a modeled camera geometry for live imaging used for re-registration of a treatment plan including 3D anatomical structures and associated instrument trajectories to the head mounted display coordinates, according to various embodiments of the disclosure.

As shown in FIG. 11, the camera geometry associated with the live imaging system imager or transducer of the second image acquisition apparatus 436 may also be modeled. For example, the modeling may include a plane or sector for intra-modality care of CT fluoroscopy (as well as the inter-modality case of sonography). Likewise, the modeling may include a projection frustum for the case of fluoroscopy. Further, the modeling may include a camera frustum for the case of endoscopy.

2. Intra-Procedure Initial Registration or Pre-Registration:

In reference to FIGS. 9 and 10, it should be appreciated that the initial registration of the planned trajectory and delineated and/or segmented anatomical structures to the augmented reality system 404 or HMD (world coordinates) can be performed using the rigid pre-registration method 100, described hereinabove. For the initial registration, the camera geometry is also registered to the HMD coordinates, either intrinsically, e.g., as in the intramodality case of CT fluoroscopy, or extrinsically, e.g., as in the case of sonography. The treatment plan and holographic live images are then both located in HMD coordinates and stored on the augmented reality system 404.

3. Refinements of the Initial Registration of Key Structures 3D Dataset to Live Imaging:

For the case of a planar or sector field-of-view, such as 2D sonography and MDCT fluoroscopy, intersection points of the segmented target tissue and the live camera field-of-view may be determined, as described more specifically in reference to the examples shown FIGS. 13-20 further herein.

Figure 12:
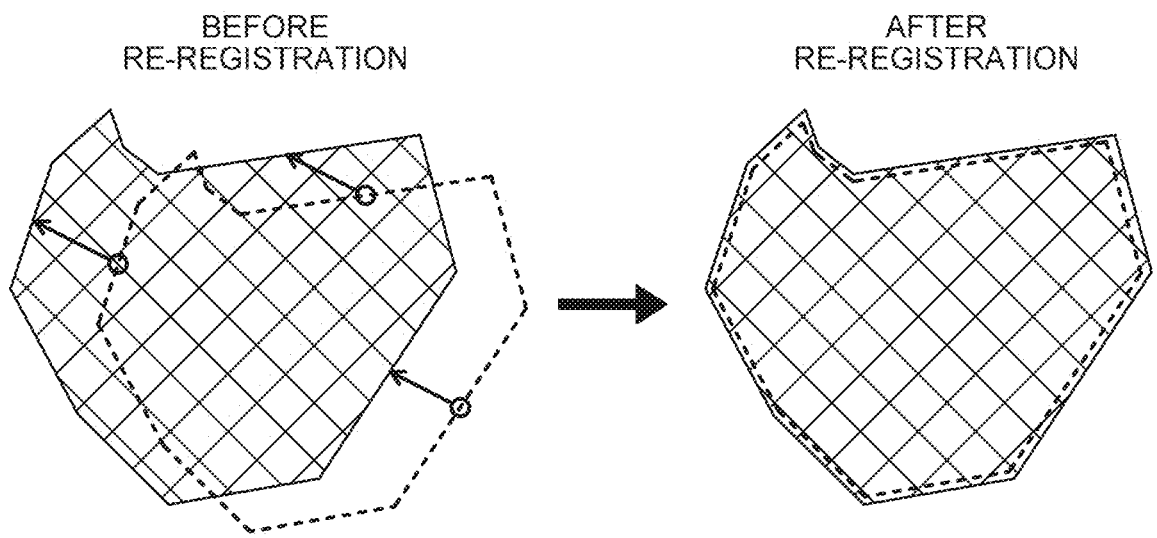
FIG. 12 is a schematic diagram showing a re-registration method with a live imaged key structure having a black solid contour, and an intersection between the 3D key structure of the treatment plan and the live image field-of-view (planar in the case) shown as a dashed contour line, where after re-registration the contours are substantially congruent and the planned trajectory accurately aligned.

Generally, however, in re-registration one or more contours may be shown on the live camera image of the augmented reality system 404, as illustrated in FIG. 12. In FIG. 12, the intersection points are shown in dashed lines with key structures such as target tissue or other critical structures shown in solid lines.

In accordance with the step 330 of FIG. 9, and associated FIGS. 10-12, the comparison may be performed between the intersection contours and the live imaging of the structure, for example, as shown at the left in FIG. 12. In a semi-automated method, the comparison can be performed visually by the operator of the augmented reality system 404. This can be performed at a breath hold or at suspension of breathing during ventilation, for example, where the movement of the patient 401 may be minimized. The transformation of the key structures in the 3D data set is then updated so that the contours align or are congruent with the live imaged structures, for example, as further shown at the right in FIG. 12.

For the case of the projective field-of-view of the camera (e.g., fluoroscopy or endoscopy), the comparison under the step 330 of the method 300 may also be made either a) in the common projection of the key structures, or b) at the intersection of the field of view delineation lines, or c) at the projection lines of key landmarks, as desired by the operator.

The re-registration transformation may then be determined manually by adjusting the 3D representation (e.g., holographic) of key structures in accordance with the step 332 of the method 300. The adjusting may be performed using hand gestures or handles on the anatomical hologram, as non-limiting examples. The transformation can also be adjusted automatically or semi-automatically. One automated method may include an incremental adjustment of the 3D translation (Tx, Ty, Tz) and rotations (Rx, Ry, Rz) by the computer, and evaluating a registration figure of merit (e.g., the Boolean intersection of the imaged edge-contour and the intersectional contour of the imaged at each increment). The incremental adjustment may be selected on each iteration that results in an improvement in the figure of merit until an optimization criterion is met. The intersection points and contours are then updated on the augmented reality system 404.

After the re-registration is performed, the contours of the live imaged key structure and the 3D key structure of the treatment plan may be substantially congruent, which is indicative of the planned trajectory being accurately aligned. Other suitable means for either manually, semi-manually, or automatically adjusting the first holographic image dataset to align with the real-time holographic image dataset from the patient to provide the re-registration transformation may also be employed, as desired.

More generally, and as set forth hereinabove, the re-registration method 300 can be used for other preliminary registration methods (i.e., re-registration is not limited to use with pre-registration). For example, the initial registration of the treatment plan (e.g., probe trajectory and rigid anatomical holograms) to HMD display coordinate may be based on a fiducial marker method instead of the pre-registration method as described hereinabove.

4. Intersectional Contours:

As set forth hereinabove, it should be appreciated that the re-registration method 300 may employ the use of intersectional contours, which are obtained by comparing the first holographic image dataset from the patient with the initial transformation to a real-time holographic image dataset of the patient during the image-guided intervention. It should be appreciated, however, that the intersectional contour technique may also have applications other than just the re-registration method. Certain examples for generating the intersectional contours for either re-registration or other applications, for example, as shown in FIGS. 13-20, are described further hereinbelow.

FIG. 13 illustrates a method 500 of image-guided intervention involving the use of intersectional contours for re-registration, as described further herein. Like or related steps from FIGS. 1, 6, 8, and 9 are shown in FIG. 13 with the same number but in a 500-series, for purpose of clarity.

In particular, the method 500 of image-guided intervention for the patient 201, 401 may include both a step 518 of acquiring with the first image acquisition apparatus 206, 406 the first holographic image dataset of the patient 201, 401, and a step 519 of acquiring with the second image acquisition apparatus 436 the second holographic image dataset of the patient 201, 401 during the image-guided intervention. In particular embodiments, the second holographic image dataset may be a real-time holographic image, and in more particular embodiments, the first holographic image dataset is a three-dimensional image and the second holographic image dataset is a two-dimensional planar sector image, both of which can be shown to the operator via the augmented reality system 204, 404.

In a step 530, the first holographic image dataset is then compared with the second holographic image dataset. For example, the comparison may include an overlaying of the first holographic image dataset with the second holographic image dataset, for example, as shown in FIGS. 12 and 14.

In a step 531, the intersectional contour of the first holographic image dataset on the second holographic image dataset may be determined. For example, the intersectional contour may be defined by intersecting points of the three-dimensional image of the first holographic image dataset and the two-dimensional planar sector of the real-time holographic image. It should be appreciated that a series of the intersecting points may define a boundary line of the intersectional contour. In certain examples, the first image acquisition apparatus 206, 406 is one of the multidetector row computerized tomography (MDCT) imager and the C-arm angio fluoroscopy imager, and the second image acquisition apparatus 436 is the ultrasound transducer.

More particularly, the step 531 of determining the intersectional contour of the first holographic image dataset on the second holographic image dataset may include calculating the portion of the first holographic image dataset that is not the intersectional contour from the view of the operator. In this case, the intersectional contour may be a vertex or mesh element retained in a stereoscopic projection, where a distance value is less than a threshold value ($\lambda$) that is preset or predetermined by the operator. It should be appreciated that the threshold value ($\lambda$) may define a dimension of the intersectional contour relative to the two-dimensional planar sector.

The threshold value ($\lambda$), and its employment in defining the dimension of the intersectional contour, is also described further in the algorithm shown in FIG. 14. The threshold value ($\lambda$) is selected to be large enough for the intersectional contour to be visually seen with the augmented reality system 204, 404, without being so large that it undesirably obstructs the view of the patient and/or the target tissue by the operator. The threshold value ($\lambda$) can also be a negative (−) or a positive (+) value, or both, as the dimension of the intersectional contour may extend on either side of the two-dimensional planar sector, as desired. It should be appreciated that, in certain examples, the threshold value ($\lambda$), has a value of between 0.1 mm and about 2 mm, and most particularly about 1 mm. However, one of ordinary skill in the art may select other suitable values for the threshold value ($\lambda$) within the scope of the present disclosure.

The step 531 further includes a step of removing, by the computer 208, 408, a portion of the first holographic image dataset that is not the intersectional contour from a view of the operator of an augmented reality system 204, 404. In this example, only the intersectional contour of the first holographic image dataset is shown overlaid on the second holographic image dataset to the operator. It should be appreciated that the threshold value ($\lambda$) may be predetermined or may be adjusted by the operator in order to show a desired dimension of the intersectional contour. The desired dimension may be one that does not adversely obstruct a view of the patient by the operator. Other suitable means for determining the intersectional contour from the comparison of the first holographic image dataset with the second holographic image dataset may also be employed, as desired.

Following the step 531, the method 500 may include a further step 532 of aligning the first holographic image dataset with the intersectional contour, whereby the re-registration transformation may be performed as set forth in the method 300 described hereinabove. Likewise, the re-registration transformation performed using the intersectional contour may be stored for further use in the image-guided intervention, as also set forth in the re-registration method 300.

5. Example of Image Guided Intervention with Intersectional Contours:

An exemplary embodiment of an intervention 600 by an operator 601 for the patient 201, 401 and utilizing the intersectional contour technology is further shown in FIGS. 15-20. In FIG. 15, the intervention 600 is shown including a three-dimensional holographic image 602 of the patient 201 compared with a real-time two-dimensional sector image 604 of the patient 201, 401. As non-limiting examples, the three-dimensional holographic image 602 of the patient 201, 401 may be obtained from the first holographic image dataset, which in turn is acquired from the first image acquisition apparatus 206, 406 such as the multidetector row computerized tomography (MDCT) imager or the C-arm angio fluoroscopy imager. Similarly, the real-time two-dimensional sector image 604 of the patient 201, 401 may be obtained from the second holographic image dataset, which in turn is acquired from the second image acquisition apparatus 436 such as the ultrasound transducer.

As further shown in FIG. 15, where an intersectional contour line 606 is initially generated, the intersectional contour line 606 may be initially offset from the real-time image (shown right in FIG. 15). In order to adjust for this inaccuracy, which may be caused by patient movement, as one non-limiting example, a location of the three-dimensional holographic image 602 of the patient 201, 401 as viewed through the augmented reality system may be adjusted as described herein.

In one example, the real-time two-dimensional sector image 604 of the patient 201, 401 may be further provided with controls 608 with which the operator 601 may interact to manually cause movement of the three-dimensional holographic image 602 of the patient 201, 401 relative to the real-time two-dimensional sector image 604. The movement may be caused by the operator until the three-dimensional holographic image 602 of the patient 201, 401 is substantially aligned or congruent with the intersectional contour line 606 (shown left in FIG. 15). As described further hereinabove, either semi-automatic or fully automatic adjustments may also be employed in lieu of the manual adjustment method, as desired.

More particularly, as shown in FIG. 16, the operator 601 may begin the intervention 600 by placing at least one optical image target 610 adjacent the patient 201, 401, or in this case a portion of the patient 201, 401, such as a breast 612 of the patient 201, 401, on which the intervention 600 is to be performed. The operator 601 may further wear the augmented reality system 204, 404 in the form of the head mounted device of the present disclosure, and view the patient 201, 401 through the augmented reality system 204, 404.

In particular, FIG. 16 shows the view of the operator 601 during an ultrasound scanning of the breast 612 of the patient with an ultrasound probe 614 being pressed against the breast 612 of the patient 201, 401. Another image target (not shown) may be used on the ultrasound probe 614, which can be used to determine a transformation from the tracked ultrasound probe 614 to the three-dimensional holographic image 602 of the patient 201, 401.

The augmented reality system 204, 404 also permits for a view of the physical interventional device 616 and an associated holographic light ray 618 to be used for the intervention 600. The at least one optical image target 610 is further shown in an offset position from the breast 612 in FIG. 16, and permitting for the employment of the augmented reality system with the intervention 600, for example, due to implementation of the pre-registration and/or re-registration methods as described hereinabove.

For the intervention 600, and as shown in FIG. 17, the operator 601 then may select with the augmented reality system 204, 404 to view the three-dimensional holographic image 602 of the patient. The three-dimensional holographic image 602 shows target tissue for the intervention 600, as well as surrounding vasculature, for example.

Further in support of the intervention 600, and as shown in FIG. 18, the operator 601 may then select with the augmented reality system 204, 404 to view the real-time two-dimensional sector image 604 of the patient. In this case, the real-time two-dimensional sector image 604 from the ultrasound scan may be overlaid with the three-dimensional holographic image 602 of the patient from the CT scan. In this case, both of the three-dimensional holographic and real-time two-dimensional sector images 602, 604 may also be provided as translucent so as to permit the operator 601 to also view the breast 612 of the patient for the intervention 600.

It should be appreciated that the operator 601 may then, as shown in FIG. 19, cause the augmented reality system 204, 404 to generate the intersectional contour lines 606 of the target tissue on the real-time two-dimensional sector image 604, i.e., the holographic ultrasound plane visualized through the augmented reality system 204, 404. As shown in FIG. 20, the intersectional contour lines 606 will also change depending on the movement of the ultrasound probe 614, such that a firmer press of the ultrasound probe 614 against the breast 612 of the patient may show the intersectional contour lines 606 at a plane through the target tissue that is different from a plane through the target tissue that may be shown with a softer press of the ultrasound probe 614 against the breast 612 of the patient.

Advantageously, the method 100 and the associated system 200 of the present disclosure enables pre-registration for 3D holographic guidance and navigation, which leads to less steps for the operator and more effective workflow. It is believed that the efficiency of the method 100 and the system 200 will facilitate increased adoption of the method 100 and the system 200. Likewise, the method 300 and the system 400 of the present disclosure, which enables intra-procedural re-registration of 3D holograms derived from 3D tomographic data with live imaging, including re-registration through use of intersectional contour techniques, is believed to improve accuracy and safety of the probe placement during interventional procedures.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A method of image-guided intervention for a patient, the method comprising steps of:
providing an installation of an augmented reality system at a first image acquisition apparatus, the augmented reality system in communication with a computer with a processor and a memory, and the augmented reality system having an augmented reality system coordinate system and the first image acquisition apparatus having a first image acquisition apparatus coordinate system, the first image acquisition apparatus further having a patient table for receiving the patient and an imager for acquiring a first holographic image dataset from the patient while on the patient table, and the installation further including steps of:
placing a first optical image target at a predetermined location on the imager;
acquiring a first optical image target coordinates from the first optical image target with the augmented reality system;
determining a pre-registration transformation of the first image acquisition apparatus coordinate system into the augmented reality system coordinate system using the first optical image target coordinates; and
storing the pre-registration transformation in the memory of the computer, whereby a pre-registration of the first image acquisition apparatus with the augmented reality system is performed; and
following the installation of the augmented reality system and the pre-registration of the first image acquisition apparatus with the augmented reality system, applying the pre-registration transformation to transform the first holographic image dataset from the first image acquisition apparatus coordinate system to the augmented reality system coordinate system, wherein applying the pre-registration transformation occurs during the image-guided intervention, the image-guided intervention including steps of:
placing a second image target on the patient while on the patient table;
acquiring a second optical image target coordinates from the second image target with the augmented reality system;
acquiring a first holographic image dataset of a portion of the patient on the patient table;
creating a surgical interventional plan using the first image acquisition apparatus, the surgical interventional plan including a delineation of target tissue in the first holographic image dataset, the surgical interventional plan provided in the first image acquisition apparatus coordinate system;
transmitting the surgical interventional plan from the first image acquisition apparatus to the augmented reality system;
transforming the surgical interventional plan from a first image acquisition apparatus coordinate system of the first image acquisition apparatus into the augmented reality system coordinate system using the pre-registration transformation from the installation; and
generating a holographic light ray on the augmented reality system to show an operator a trajectory for an instrument according to the surgical interventional plan.

2. The method of claim 1, wherein the step of acquiring the first optical image target coordinates from the first optical image target with the augmented reality system includes moving the augmented reality system so that the first optical image target is in a field of view of the augmented reality system.

3. The method of claim 1, wherein the patient table is translatable, and further comprising at least one of:
determining and registering a position of the patient table with the augmented reality system;
placing an additional image target at the patient table, acquiring an additional image target dataset from the additional image target with the augmented reality system, and determining a position of the patient table by the augmented reality system based on the additional image target dataset; and
transmitting a position of the patient table from a patient table sensor on the patient table to the augmented reality system.

4. The method of claim 1, further comprising a re-registration to compensate the pre-registration transformation for inaccuracy.

5. The method of claim 4, wherein the re-registration includes steps of:
acquiring with the first image acquisition apparatus a real-time holographic image dataset of the patient during the image-guided intervention;
comparing the real-time holographic image dataset with the patient or the first holographic image dataset; and
adjusting the first holographic image dataset to align with the real-time holographic image dataset from the patient.

6. The method of claim 5, wherein the first holographic image dataset defines a three-dimensional image volume and the real-time holographic image dataset defines a two-dimensional planar sector.

7. The method of claim 6, wherein the portion of the first holographic image dataset is an intersectional contour defined by intersection points of the three-dimensional image volume of the first holographic image dataset and the two-dimensional planar sector of the real-time holographic image dataset.

8. A system of image-guided intervention for a patient, comprising:
an installation of an augmented reality system at a first image acquisition apparatus, the augmented reality system in communication with a computer with a processor and a memory, and augmented reality system having an augmented reality system coordinate system and the first image acquisition apparatus having a first image acquisition apparatus coordinate system, the first image acquisition apparatus further having a patient table for receiving the patient and an imager for acquiring a first holographic image dataset from the patient while on the patient table,
wherein a pre-registration transformation is stored in the memory of the computer, the pre-registration transformation determined by steps of:
placing a first optical image target at a predetermined location on the imager;
acquiring a first optical image target coordinates from the first optical image target with the augmented reality system; and
determining a pre-registration transformation of the first image acquisition apparatus coordinate system into the augmented reality system coordinate system using the first optical image target coordinates,
wherein the pre-registration transformation occurs during the image-guided intervention, the image-guided intervention further determined by steps of:
placing a second image target on the patient while on the patient table;
acquiring a second optical image target coordinates from the second image target with the augmented reality system;
acquiring a first holographic image dataset of a portion of the patient on the patient table;
creating a surgical interventional plan using the first image acquisition apparatus, the surgical interventional plan including a delineation of target tissue in the first holographic image dataset, the surgical interventional plan provided in the first image acquisition apparatus coordinate system;

transmitting the surgical interventional plan from the first image acquisition apparatus to the augmented reality system;

transforming the surgical interventional plan from a first image acquisition apparatus coordinate system of the first image acquisition apparatus into the augmented reality system coordinate system using the pre-registration transformation from the installation; and generating a holographic light ray on the augmented reality system to show an operator a trajectory for an instrument according to the surgical interventional plan.

9. A method of image-guided intervention for a patient, the method comprising steps of:

providing an installation of an augmented reality system at a first image acquisition apparatus, the augmented reality system in communication with a computer with a processor and a memory, and the augmented reality system having an augmented reality system coordinate system and the first image acquisition apparatus having a first image acquisition apparatus coordinate system, an initial transformation of the first image acquisition apparatus coordinate system into the augmented reality system coordinate system stored in the memory of the computer, the first image acquisition apparatus further having a patient table for receiving a patient and an imager for acquiring a first holographic image dataset from the patient while on the patient table, acquiring with the first image acquisition apparatus a real-time holographic image dataset of the patient during the image-guided intervention;

comparing the real-time holographic image dataset with the patient or the first holographic image dataset;

adjusting the first holographic image dataset to align with the real-time holographic image dataset from the patient to provide a re-registration transformation; and storing the re-registration transformation in the memory of the computer, wherein:

the initial transformation is a pre-registration transformation determined by the steps of:

placing a first optical image target at a predetermined location on the imager;

acquiring a first optical image target coordinates from the first optical image target with the augmented reality system; and determining a pre-registration transformation of the first image acquisition apparatus coordinate system into the augmented reality system coordinate system using the first optical image target coordinates, the first holographic image dataset is a three-dimensional image and the real-time holographic image dataset is a two-dimensional planar sector, and a portion of the first holographic image dataset is an intersectional contour, the intersectional contour defined by intersection points of the three-dimensional image of the first holographic image dataset and the two-dimensional planar sector of the real-time holographic image dataset.

10. A system of image-guided intervention for a patient, comprising:

an installation of an augmented reality system at a first image acquisition apparatus, the augmented reality system in communication with a computer with a processor and a memory, and the augmented reality system having an augmented reality system coordinate system and the first image acquisition apparatus having a first image acquisition apparatus coordinate system, an initial transformation of the first image acquisition apparatus coordinate system into the augmented reality system coordinate system stored in the memory of the computer, the first image acquisition apparatus further having a patient table for receiving the patient and an imager for acquiring a first holographic image dataset from the patient while on the patient table, wherein a re-registration transformation is stored in the memory of the computer, the re-registration transformation determined by steps of:

acquiring with the first image acquisition apparatus a real-time holographic image dataset of the patient during the image-guided intervention;

comparing the real-time holographic image dataset with the patient or the first holographic image dataset; and adjusting the first holographic image dataset to align with the real-time holographic image dataset from the patient to provide the re-registration transformation, wherein:

the initial transformation is a pre-registration transformation determined by the steps of:

placing a first optical image target at a predetermined location on the imager;

acquiring a first optical image target coordinates from the first optical image target with the augmented reality system; and determining a pre-registration transformation of the first image acquisition apparatus coordinate system into the augmented reality system coordinate system using the first optical image target coordinates, the first holographic image dataset is a three-dimensional image and the real-time holographic image dataset is a two-dimensional planar sector, and a portion of the first holographic image dataset is an intersectional contour, the intersectional contour defined by intersection points of the three-dimensional image of the first holographic image dataset and the two-dimensional planar sector of the real-time holographic image dataset.

11. A method of image-guided intervention for a patient, the method comprising steps of:

acquiring a first holographic image dataset of the patient and a second holographic image dataset of the patient during the image-guided intervention;

comparing the first holographic image dataset with the second holographic image dataset by overlaying the first holographic image dataset with the second holographic image dataset;

determining an intersectional contour of the first holographic image dataset on the second holographic image dataset; and removing a portion of the first holographic image dataset that is not the intersectional contour from a view of an operator of an augmented reality system, whereby only the intersectional contour of the first holographic image dataset is shown overlaid on the second holographic image dataset, wherein:

the second holographic image dataset is a real-time holographic image, the first holographic image dataset is a three-dimensional image and the second holographic image dataset is a two-dimensional planar sector, the intersectional contour is defined by intersection points of the three-dimensional image of the first holographic image dataset and the two-dimensional planar sector of the real-time holographic image, and the step of determining the intersectional contour of the first holographic image dataset on the second holographic image dataset includes determining the portion of the first holographic image dataset that is not the intersectional contour from the view of the operator, the intersectional contour being a vertex or mesh element retained in a stereoscopic projection where a distance value is less than a threshold value ($\lambda$) preset by the operator, the threshold value defining a dimension of the intersectional contour relative to the two-dimensional planar sector.

12. The method of claim 11, further including a step of adjusting the threshold value ($\lambda$) by the operator in order to show the intersectional contour without adversely obstructing a view of the patient by the operator.

13. A system of image-guided intervention for a patient, comprising:

an installation of an augmented reality system at a first image acquisition apparatus, the augmented reality system in communication with a computer with a processor and a memory, and the augmented reality system having an augmented reality system coordinate system and the first image acquisition apparatus having a first image acquisition apparatus coordinate system, an initial transformation of the first image acquisition apparatus coordinate system into the augmented reality system coordinate system stored in the memory of the computer, the first image acquisition apparatus further having a patient table for receiving the patient and an imager for acquiring a first holographic image dataset from the patient while on the patient table; and wherein an intersectional contour is shown on the augmented reality system, the intersectional contour determined by steps of:

acquiring with the first image acquisition apparatus the first holographic image dataset of the patient;

acquiring a second holographic image dataset of the patient during the image-guided intervention;

comparing the first holographic image dataset with the second holographic image dataset by overlaying the first holographic image dataset with the second holographic image dataset;

determining the intersectional contour of the first holographic image dataset on the second holographic image dataset; and removing a portion of the first holographic image dataset that is not the intersectional contour from a view of an operator of the augmented reality system, whereby only the intersectional contour of the first holographic image dataset is shown overlaid on the second holographic image dataset.

* * * * *